US010335365B2

(12) United States Patent
Pan et al.

(10) Patent No.: US 10,335,365 B2
(45) Date of Patent: *Jul. 2, 2019

(54) BLADDER CANCER SPECIFIC LIGAND PEPTIDES

(71) Applicant: The Regents of the University of California, Oakland, CA (US)

(72) Inventors: Chong-Xian Pan, Davis, CA (US); Hongyong Zhang, Davis, CA (US); Kit S. Lam, Davis, CA (US); Olulanu H. Aina, Elk Grove, CA (US)

(73) Assignees: The Regents ot the Univershy of California, Oakland, CA (US); The United States of America as represented by the Department of Veteran Affairs (Washington DC), Washington, DC (US)

( * ) Notice: Subject to any disclaimer, the term of this patent is extended or adjusted under 35 U.S.C. 154(b) by 5 days.

This patent is subject to a terminal disclaimer.

(21) Appl. No.: 15/400,987

(22) Filed: Jan. 7, 2017

(65) Prior Publication Data

US 2017/0173174 A1    Jun. 22, 2017

Related U.S. Application Data

(60) Continuation of application No. 14/589,680, filed on Jan. 5, 2015, now Pat. No. 9,539,340, which is a division of application No. 13/497,041, filed as application No. PCT/US2010/050037 on Sep. 23, 2010, now Pat. No. 8,946,379.

(60) Provisional application No. 61/245,492, filed on Sep. 24, 2009.

(51) Int. Cl.
| | |
|---|---|
| A61K 39/00 | (2006.01) |
| A61K 9/00 | (2006.01) |
| A61K 49/00 | (2006.01) |
| B82Y 5/00 | (2011.01) |
| C07K 7/06 | (2006.01) |
| G01N 33/574 | (2006.01) |
| A61K 51/08 | (2006.01) |
| A61K 9/51 | (2006.01) |
| A61K 47/51 | (2017.01) |
| A61K 47/64 | (2017.01) |
| A61K 47/66 | (2017.01) |
| A61K 38/00 | (2006.01) |

(52) U.S. Cl.
CPC ............ *A61K 9/0019* (2013.01); *A61K 9/51* (2013.01); *A61K 47/51* (2017.08); *A61K 47/64* (2017.08); *A61K 47/66* (2017.08); *A61K 49/0002* (2013.01); *A61K 49/0032* (2013.01); *A61K 49/0056* (2013.01); *A61K 51/088* (2013.01); *B82Y 5/00* (2013.01); *C07K 7/06* (2013.01); *G01N 33/57407* (2013.01); *A61K 38/00* (2013.01)

(58) Field of Classification Search
None
See application file for complete search history.

(56) References Cited

U.S. PATENT DOCUMENTS

| | | |
|---|---|---|
| 8,946,379 B2 | 2/2015 | Pan et al. |
| 9,539,340 B2 | 1/2017 | Pan et al. |
| 2005/0260581 A1 | 11/2005 | Fontana et al. |
| 2007/0196366 A1 | 8/2007 | Zangemeister-Wittke et al. |
| 2008/0139479 A1 | 6/2008 | Ruoslahti et al. |
| 2012/0230994 A1 | 9/2012 | Pan et al. |
| 2015/0190527 A1 | 7/2015 | Pan et al. |

FOREIGN PATENT DOCUMENTS

| | | |
|---|---|---|
| CN | 1464058 A | 12/2003 |
| CN | 1610743 A | 4/2005 |
| CN | 102639555 B | 8/2012 |
| EP | 2480563 B1 | 2/2017 |
| JP | 5875518 B2 | 1/2016 |
| TW | I494566 | 8/2015 |
| WO | WO 2001/72958 | 10/2001 |
| WO | WO 2005/045430 | 5/2005 |
| WO | WO 2006/067633 | 6/2006 |
| WO | WO 2009/090651 | 7/2009 |
| WO | WO 2009/113674 | 9/2009 |
| WO | WO 2011/038142 | 3/2011 |

OTHER PUBLICATIONS

Indian First Office Action [Examination Report] dated Feb. 16, 2018 issued in IN 695/MUMNP/2012.
U.S. Office Action (Requirement for Restriction/Election) dated May 31, 2013 issued in U.S. Appl. No. 13/497,041.
U.S. Office Action dated Nov. 14, 2013 issued in U.S. Appl. No. 13/497,041.
U.S. Notice of Allowance dated Mar. 6, 2014 issued in U.S. Appl. No. 13/497,041.
U.S. Notice of Allowance dated Jul. 2, 2014 issued in U.S. Appl. No. 13/497,041.
U.S. Notice of Allowance dated Oct. 3, 2014 issued in U.S. Appl. No. 13/497,041.

(Continued)

*Primary Examiner* — Lei Yao
(74) *Attorney, Agent, or Firm* — Mintz, Levin, Cohn, Ferris, Glovsky and Popeo, P.C.

(57) ABSTRACT

The present invention is directed to bladder cancer specific ligand peptides, comprising the amino acid sequence $X_1DGRX_5GF$ (SEQ ID NO: 1), and methods of their use, e.g., for imaging detection for diagnosis of bladder, tumor localization to guide transurethral resection of bladder cancer, imaging detection of bladder cancer for follow-up after the initial treatment that can replace or complement costly cystoscopy, imaging detection of metastatic bladder cancer, and targeted therapy for superficial and metastatic bladder cancer.

40 Claims, 15 Drawing Sheets

Specification includes a Sequence Listing.

(56) References Cited

OTHER PUBLICATIONS

U.S. Notice of Allowance dated Jan. 5, 2015 issued in U.S. Appl. No. 13/497,041.
U.S. Office Action (Requirement for Restriction/Election) dated Mar. 29, 2016 issued in U.S. Appl. No. 14/589,680.
U.S. Notice of Allowance dated Sep. 14, 2016 issued in U.S. Appl. No. 14/589,680.
PCT International Search Report and Written Opinion dated Jun. 27, 2011 issued in PCT/US2010/050037.
PCT International Preliminary Report on Patentability dated Mar. 27, 2012 issued in PCT/US2010/050037.
European Extended Search Report dated Mar. 21, 2014 issued in EP10819475.4.
European Office Action dated Apr. 28, 2015 issued in EP 10 819 475.4.
European Office Action [Intention to Grant] dated Jun. 29, 2016 issued in EP 10 819 475.4.
European Office Action [Decision to Grant] dated Jan. 26, 2017 issued in EP 10 819 475.4.
Chinese First Office Action [Description in English] dated Jun. 28, 2013 issued in CN 201080052434.6.
Chinese Second Office Action [Description in English] dated May 12, 2014 issued in CN 201080052434.6.
Chinese Third Office Action [Description in English] dated Nov. 26, 2014 issued in CN 201080052434.6.
Japanese Notice for Reasons for Rejection dated Dec. 15, 2014 issued in JP 2012-531034.
Japanese Decision of Rejection dated Jul. 8, 2015 issued in JP 2012-531034.
Korean Office Action dated Feb. 23, 2017 issued in KR 10-2012-7010557.
Taiwan Office Action dated Aug. 11, 2014 issued in TW 099132256.
Aina et al. (2007) "From Combinatorial Chemistry to Cancer-Targeting Peptides" *Molecular Pharmaceutics* 4(5):631-651.
AJCC Cancer Staging Manual, 5th Edition, Lippincott-Raven Publishers, Philadelphia, New York (1997), 324 pages.
Asokan, et al. (Sep. 2006) "Adeno-Associated Virus Type 2 Contains an Integrin α5β1 Binding Domain Essential for Viral Cell Entry," *Journal of Virology* 80(18):8961-8969.
Bagai, et al. (2002) "Fibroblast Growth Factor-10 is a Mitogen for Urothelial Cells," *The Journal of Biological Chemistry* 277(26):23828-23837.
Botteman, et al. (2003) "The Health Economics of Bladder Cancer," *Pharmacoeconomics* 21(18):1315-1330.
Chuman, et al. (2004) "Identification of a peptide binding motif for secreted frizzled-related protein-1," *Peptides* 25:1831-1838.
Cookson, et al. (Jul. 1997) "The Treated Natural History of High Risk Superficial Bladder Cancer: 15-Year Outcome," *The Journal of Urology* 158:62-67.
Daniltchenko, et al. (2005) "Long-Term Benefit of 5-Aminolevulinic Acid Fluorescence Assisted Transurethral Resection of Superficial Bladder Cancer: 5-Year Results of a Prospective Randomized Study," *The Journal of Urology* 174:2129-2133.
Drieskens, et al. (2005) "FDG-PET for preoperative staging of bladder cancer," *Eur J Nucl Med Mol Imaging* 32:1412-1417.
Eissa, et al. (2003) "Detection of bladder tumours: role of cytology, morphology-based assays, biochemical and molecular markers," *Current Opinion in Obstetrics and Gynecology* 15:395-403.
Herr, et al. (1989) "Superficial Bladder Cancer Treated With Bacillus Calmette-Guerin: A Multivariate Analysis of Factors Affecting Tumor Progression," *The Journal of Urology* 141:22-29 [5 pages].
Herr, et al. (1995) "Intravesical Bacillus Calmette-Guerin Therapy Prevents Tumor Progression and Death From Superficial Bladder Cancer: Ten-Year Follow-Up of a Prospective Randomized Trial," *Journal of Clinical Oncology* 13(6):1404-1408.
Herr, et al. (2005) "Restaging Transurethral Resection of High Risk Superficial Bladder Cancer Improves the Initial Response to Bacillus Calmette-Guerin Therapy," *The Journal of Urology* 174: 2134-2137.
Jemal, et al. (2008) "Cancer Statistics," *CA Cancer J Clin* 158:71-96.
Koivunen, et al. (1993) "Selection of Peptides Binding to the α5β1 Integrin from Phage Display Library," *The Journal of Biological Chemistry* 266(27):20205-20210.
Koivunen, et al. (1994) "Isolation of a Highly Specific Ligand for the α5β1 Integrin from a Phage Display Library," *The Journal of Cell Biology* 124(3):373-380.
Lam, et al. (1997) "The "One-Bead-One-Compound" Combinatorial Library Method," *Chem. Rev.* 97:411-448.
Lam, et al. (Nov. 7, 1991) "A new type of synthetic peptide library for identifying ligand-binding activity," *Nature* 354:82-84.
Lee et al. (2007) "Targeting Bladder Tumor Cells in vivo and in the Urine with a Peptide Identified by Phage Display" *Mol Cancer Res* 5(1): 11-19.
Lin et al. (2011) "Targeting canine bladder transitional cell carcinoma with a human bladder cancer-specific ligand" *Molecular Cancer* 10(9):1-6.
Lin et al. (2012) "Multifunctional targeting micelle nanocarriers with both imaging and therapeutic potential for bladder cancer" *International Journal of Nanomedicine* 7:2793-2804.
Lin et al. (2013) "Tumor-targeting multifunctional micelles for imaging and chemotherapy of advanced bladder cancer." *Nanomedicine* (Lond). 8(8):1239-1251 [Abstract Only] One Page.
Litynska, et al. (2000) "Differences of α3β1 integrin glycans from different human bladder cell lines," *Acta Biochimica Polonica* 47(2):427-434.
Liu, et al. (2002) "A Novel Peptide-Based Encoding System for 'One-Bead One-Compound' Peptidomimetic and Small Molecule Combinatorial Libraries," *J. Am. Chem. Soc.* 124(60):7678-7680.
Liu, et al. (2006) "Evaluation of Fluorodeoxyglucose Positron Emission Tomography Imaging in Metastatic Transitional Cell Carcinoma with and without Prior Chemotherapy," *Urol Int*, 77:69-75, DOI: 10.1159/000092937.
Lotan, et al. (2003) "Sensitivity and Specificity of Commonly Available Bladder Tumor Markers Versus Cytology: Results of a Comprehensive Literature Review and Meta-Analyses," *Urology* 61(1):109-118.
Luo, et al. (2008) "Rainbow Beads: A Color Coding Method to Facilitate High-Throughput Screening and Optimization of One-Bead One-Compound Combinatorial Libraries," *J. Comb. Chem.* 10:599-604.
Morini, et al. (2000) "The α3β1 Integrin Is Associated With Mammary Carcinoma Cell Metastasis, Invasion, and Gelatinase B (MMP-9) Activity," *J Int. J. Cancer* 87:336-342.
Nierman et al. (2004) "Structural flexibility in the *Burkholderia mallei* genome," *PNAS* 101(39):1426-14251.
Peng, et al. (Jul. 2006) "A Combinatorial chemistry identifies high-affinity peptidomimetics against α4β1 integrin for in vivo tumor imaging," *Nature Chemical Biology* 2(7):381-389.
Riley, et al. (Aug. 1995) "Medicare Payments from Diagnosis to Death for Elderly Cancer Patients by Stage at Diagnosis," *Medical Care* 33(8):828-841.
Songyang, et al. (1995) "The Phosphotyrosine Interaction Domain of SHC Recognizes Tyrosine-phosphorylated NPXY Motif," *The Journal of Biological Chemistry* 270(25):14863-14866.
van Rhijn, et al. (2005) "UrineMarkers for Bladder Cancer Surveillance: A Systematic Review," *European Urology* 47:736-748.
Wang, et al. (2010) "Photothermal Effects of Supramolecularly Assembled Gold Nanoparticles for the Targeted Treatment of Cancer Cells," *Angew. Chem. Int. Ed.* 49:3777-3781.
Zhang et al. (2012) "Identification of a bladder cancer-specific ligand using a combinatorial chemistry approach" *Urologic Oncology* 30(5):635-645 [doi: 10.1016/j.urolonc.2010.06.011. Epub Oct. 2, 2010].

*Figure 1*
T24 c U/Z, 19hrs      SCABER, cX7c, 45min
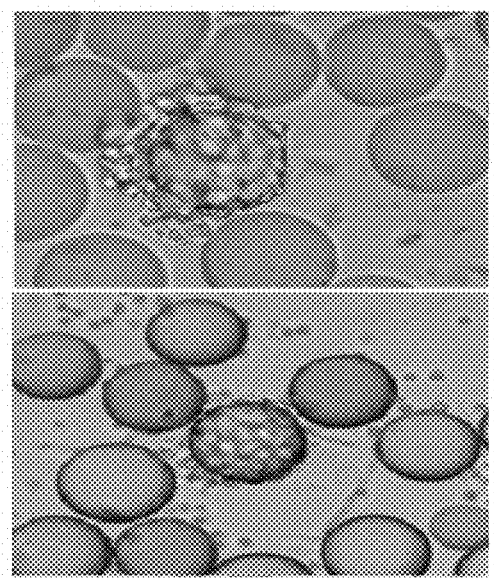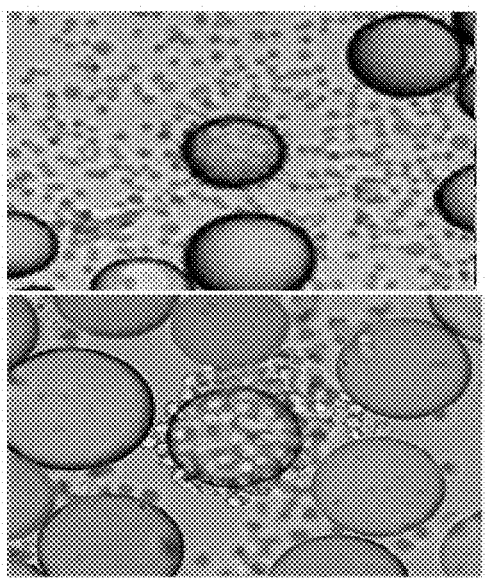
TCCSUP, cX7c, 45min      5637, cX7c, 45min

*Figures 2A-H*
| Figure 2A | Figure 2B | Figure 2C | Figure 2D |
|---|---|---|---|
| 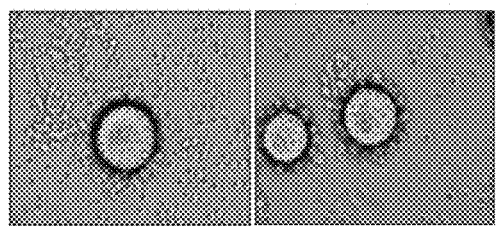 | 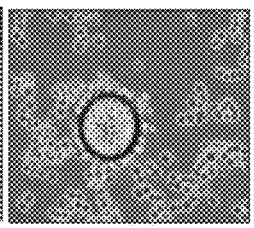 | 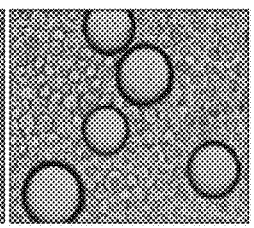 | |
| 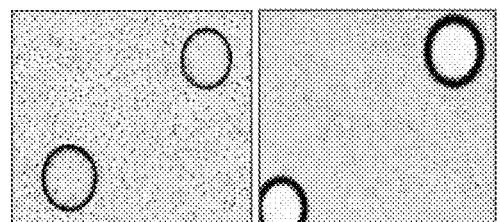 | 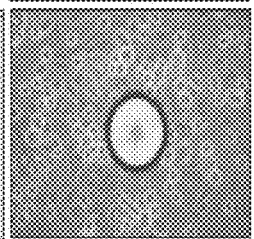 | 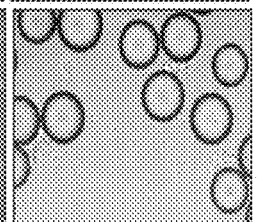 | |
| Figure 2E | Figure 2F | Figure 2G | Figure 2H |

*Figures 3A-E*

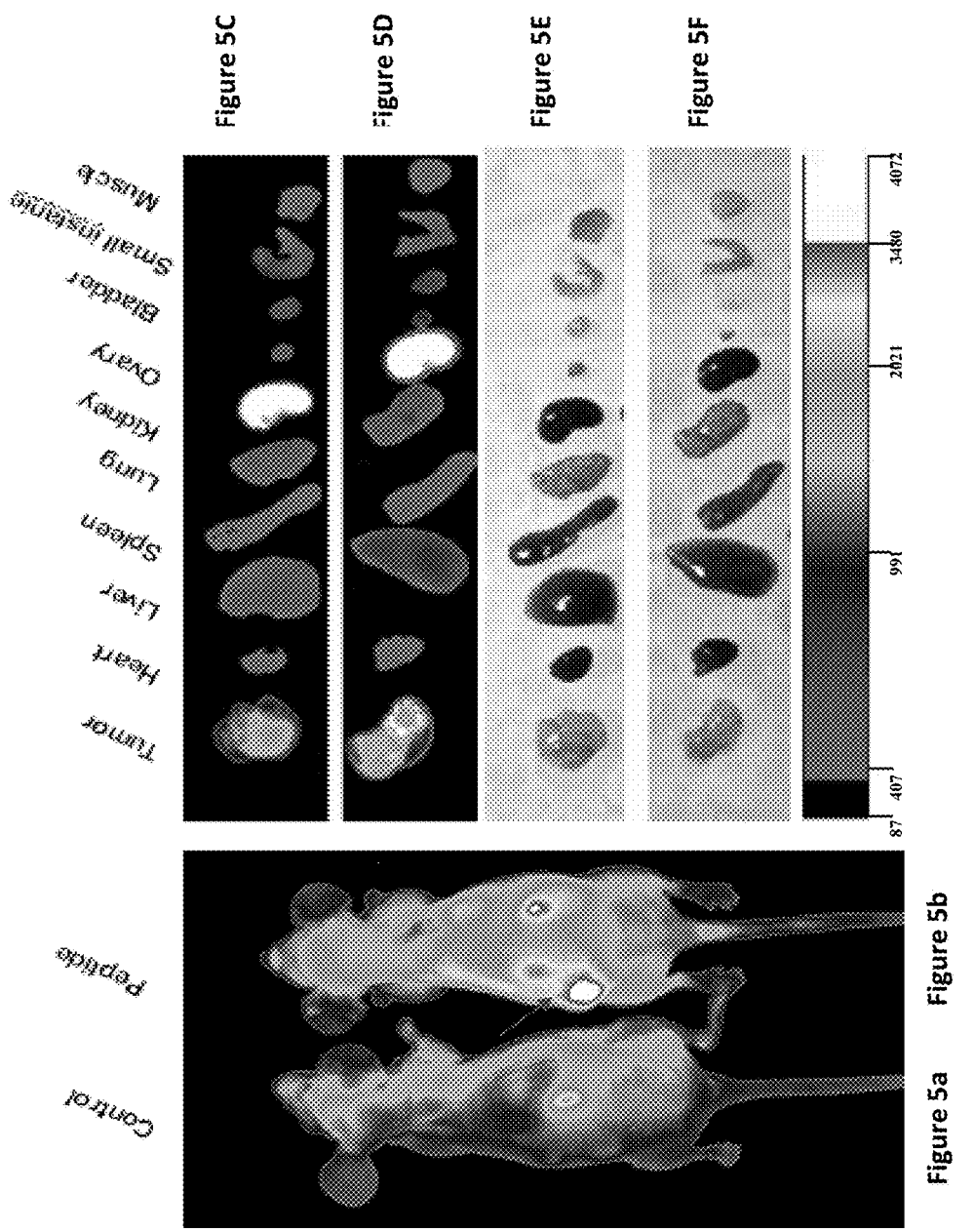
Figures 5A-F

SEQUENCE LISTING

```
<160> NUMBER OF SEQ ID NOS: 30

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any of the twenty natural amino acids except
```

```
        Cys
<220> FEATURE:
<221> NAME/KEY: MOD_RES
<222> LOCATION: (5)..(5)
<223> OTHER INFORMATION: Any of the twenty natural amino acids except
      Cys
<220> FEATURE:
<223> OTHER INFORMATION: See specification as filed for detailed
      description of substitutions and preferred embodiments

<400> SEQUENCE: 1

Xaa Asp Gly Arg Xaa Gly Phe
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Gly or Ala
<220> FEATURE:
<221> NAME/KEY: MOD_RES
<222> LOCATION: (5)..(5)
<223> OTHER INFORMATION: Any of the twenty natural amino acids except
      Cys

<400> SEQUENCE: 2

Xaa Asp Gly Arg Xaa Gly Phe
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(6)
<223> OTHER INFORMATION: The region may encompass Met, Lys, Gly, Ala or
      Gly-Gly

<400> SEQUENCE: 3

Xaa Asp Gly Arg Xaa Xaa Gly Phe
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Gly or Ala
<220> FEATURE:
<221> NAME/KEY: MOD_RES
<222> LOCATION: (5)..(6)
<223> OTHER INFORMATION: The region may encompass Met, Lys, Gly, Ala or
      Gly-Gly
```

```
<400> SEQUENCE: 4

Xaa Asp Gly Arg Xaa Xaa Gly Phe
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Asp Gly Arg Met Gly Phe
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Asp Gly Arg Lys Gly Phe
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys with a side chain Gly residue
<220> FEATURE:
<223> OTHER INFORMATION: See specification as filed for detailed
      description of substitutions and preferred embodiments

<400> SEQUENCE: 7

Gln Asp Gly Arg Lys Gly Phe
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any of the twenty natural amino acids and this
      region may encompass 1 to 5 residues or is absent
<220> FEATURE:
<221> NAME/KEY: MOD_RES
<222> LOCATION: (6)..(6)
<223> OTHER INFORMATION: Any of the twenty natural amino acids except
      Cys
<220> FEATURE:
<221> NAME/KEY: MOD_RES
<222> LOCATION: (10)..(10)
<223> OTHER INFORMATION: Any of the twenty natural amino acids except
      Cys
<220> FEATURE:
<221> NAME/KEY: MOD_RES
```

<222> LOCATION: (13)..(17)
<223> OTHER INFORMATION: Any of the twenty natural amino acids and this
      region may encompass 1 to 5 residues or is absent

<400> SEQUENCE: 8

Xaa Xaa Xaa Xaa Xaa Xaa Asp Gly Arg Xaa Gly Phe Xaa Xaa Xaa Xaa
1               5                   10                  15

Xaa

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any of the twenty natural amino acids or absent
<220> FEATURE:
<221> NAME/KEY: MOD_RES
<222> LOCATION: (3)..(3)
<223> OTHER INFORMATION: Any of the twenty natural amino acids except
      Cys
<220> FEATURE:
<221> NAME/KEY: MOD_RES
<222> LOCATION: (7)..(7)
<223> OTHER INFORMATION: Any of the twenty natural amino acids except
      Cys
<220> FEATURE:
<221> NAME/KEY: MOD_RES
<222> LOCATION: (10)..(11)
<223> OTHER INFORMATION: Any of the twenty natural amino acids or absent

<400> SEQUENCE: 9

Xaa Xaa Xaa Asp Gly Arg Xaa Gly Phe Xaa Xaa
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (2)..(2)
<223> OTHER INFORMATION: Any of the twenty natural amino acids except
      Cys
<220> FEATURE:
<221> NAME/KEY: MOD_RES
<222> LOCATION: (6)..(6)
<223> OTHER INFORMATION: Any of the twenty natural amino acids except
      Cys
<220> FEATURE:
<221> NAME/KEY: MOD_RES
<222> LOCATION: (9)..(9)
<223> OTHER INFORMATION: D-Cys

<400> SEQUENCE: 10

Cys Xaa Asp Gly Arg Xaa Gly Phe Cys
1               5

<210> SEQ ID NO 11
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (9)..(9)
<223> OTHER INFORMATION: D-Cys

<400> SEQUENCE: 11

Cys Gln Asp Gly Arg Lys Gly Phe Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (9)..(9)
<223> OTHER INFORMATION: D-Cys

<400> SEQUENCE: 12

Cys Gln Asp Gly Arg Met Gly Phe Cys
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (6)..(6)
<223> OTHER INFORMATION: Lys with a side chain of 1 to 6 Gly residues
<220> FEATURE:
<221> NAME/KEY: MOD_RES
<222> LOCATION: (8)..(8)
<223> OTHER INFORMATION: D-Cys

<400> SEQUENCE: 13

Cys Gln Asp Gly Arg Lys Phe Cys
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Gln Asp Gly Arg Met Gly Phe Cys
1               5
```

```
<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (2)..(8)
<223> OTHER INFORMATION: Any of the twenty natural L-amino acids except
      Cys
<220> FEATURE:
<221> NAME/KEY: MOD_RES
<222> LOCATION: (9)..(9)
<223> OTHER INFORMATION: D-Cys
<220> FEATURE:
<223> OTHER INFORMATION: See specification as filed for detailed
      description of substitutions and preferred embodiments

<400> SEQUENCE: 15

Cys Xaa Xaa Xaa Xaa Xaa Xaa Xaa Cys
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (2)..(6)
<223> OTHER INFORMATION: Any unnatural amino acid or any of the twenty
      natural L-amino acids except Arg, Cys or Lys
<220> FEATURE:
<221> NAME/KEY: MOD_RES
<222> LOCATION: (7)..(7)
<223> OTHER INFORMATION: D-Cys
<220> FEATURE:
<223> OTHER INFORMATION: See specification as filed for detailed
      description of substitutions and preferred embodiments

<400> SEQUENCE: 16

Cys Xaa Xaa Xaa Xaa Xaa Cys
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any of the twenty natural amino acids except
      Cys
<220> FEATURE:
<221> NAME/KEY: MOD_RES
<222> LOCATION: (6)..(6)
<223> OTHER INFORMATION: Any of the twenty natural amino acids except
      Cys
```

-continued

```
<220> FEATURE:
<223> OTHER INFORMATION: See specification as filed for detailed
      description of substitutions and preferred embodiments

<400> SEQUENCE: 17

Cys Xaa Asp Gly Arg Xaa Gly Phe Cys
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<223> OTHER INFORMATION: See specification as filed for detailed
      description of substitutions and preferred embodiments

<400> SEQUENCE: 18

Xaa Asp Gly Arg Xaa Gly Phe
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Gly or Ala
<220> FEATURE:
<221> NAME/KEY: MOD_RES
<222> LOCATION: (5)..(5)
<223> OTHER INFORMATION: Any amino acid

<400> SEQUENCE: 19

Xaa Asp Gly Arg Xaa Gly Phe
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (9)..(9)
```

```
<223> OTHER INFORMATION: D-Cys
<220> FEATURE:
<223> OTHER INFORMATION: See specification as filed for detailed
      description of substitutions and preferred embodiments

<400> SEQUENCE: 20

Cys Xaa Asp Gly Arg Xaa Gly Phe Cys
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any of the twenty natural amino acids except
      Cys
<220> FEATURE:
<221> NAME/KEY: MOD_RES
<222> LOCATION: (5)..(6)
<223> OTHER INFORMATION: The region may encompass Met, Lys, Gly, Ala or
      Gly-Gly

<400> SEQUENCE: 21

Xaa Asp Gly Arg Xaa Xaa Gly Phe
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any of the twenty natural amino acids and this
      region may encompass 1 to 5 residues
<220> FEATURE:
<221> NAME/KEY: MOD_RES
<222> LOCATION: (6)..(6)
<223> OTHER INFORMATION: Any of the twenty natural amino acids except
      Cys
<220> FEATURE:
<221> NAME/KEY: MOD_RES
<222> LOCATION: (10)..(10)
<223> OTHER INFORMATION: Any of the twenty natural amino acids except
      Cys
<220> FEATURE:
<221> NAME/KEY: MOD_RES
<222> LOCATION: (13)..(17)
<223> OTHER INFORMATION: Any of the twenty natural amino acids and this
      region may encompass 1 to 5 residues

<400> SEQUENCE: 22

Xaa Xaa Xaa Xaa Xaa Xaa Asp Gly Arg Xaa Gly Phe Xaa Xaa Xaa Xaa
1               5                   10                  15

Xaa

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(2)
<223> OTHER INFORMATION: Any of the twenty natural amino acids
<220> FEATURE:
<221> NAME/KEY: MOD_RES
<222> LOCATION: (3)..(3)
<223> OTHER INFORMATION: Any of the twenty natural amino acids except
      Cys
<220> FEATURE:
<221> NAME/KEY: MOD_RES
<222> LOCATION: (7)..(7)
<223> OTHER INFORMATION: Any of the twenty natural amino acids except
      Cys
<220> FEATURE:
<221> NAME/KEY: MOD_RES
<222> LOCATION: (10)..(11)
<223> OTHER INFORMATION: Any of the twenty natural amino acids

<400> SEQUENCE: 23

Xaa Xaa Xaa Asp Gly Arg Xaa Gly Phe Xaa Xaa
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Asp Gly Arg Met Gly Phe
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ala Gly Arg Met Gly Phe
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Asp Ala Arg Met Gly Phe
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Asp Gly Ala Met Gly Phe
1               5
```

```
<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Asp Gly Arg Ala Gly Phe
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Asp Gly Arg Met Ala Phe
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Asp Gly Arg Met Gly Ala
1               5
```

BLADDER CANCER SPECIFIC LIGAND PEPTIDES

CROSS-REFERENCE TO RELATED APPLICATIONS

The present application is a continuation of U.S. application Ser. No. 14/589,680, filed on Jan. 5, 2015 and issued on Jan. 10, 2017 as U.S. Pat. No. 9,539,340, which is a divisional of U.S. application Ser. No. 13/497,041, filed on May 31, 2012 and issued on Feb. 3, 2015 as U.S. Pat. No. 8,946,379, which is a U.S. national phase filing under 35 U.S.C. § 371 of International Appl. No. PCT/US10/050037, filed on Sep. 23, 2010, which claims the benefit of U.S. Provisional Application No. 61/245,492, filed on Sep. 24, 2009, all of which are hereby incorporated herein by reference in their entireties for all purposes.

FIELD OF THE INVENTION

The present invention is directed to bladder cancer specific ligand peptides, comprising the amino acid sequence $X_1DGRX_5GF$ (SEQ ID NO: 1), and methods of their use, e.g., for imaging detection for diagnosis of bladder, tumor localization to guide transurethral resection of bladder cancer, imaging detection of bladder cancer for follow-up after the initial treatment that can replace or complement costly cystoscopy, imaging detection of metastatic bladder cancer, and targeted therapy for superficial and metastatic bladder cancer.

BACKGROUND OF THE INVENTION

Bladder cancer is the fourth most common cancer in men and ninth in women (Jemal, et al., *Cancer J Clin*, (2008) 58: 71-96). At diagnosis, about 75% of patients are at the non-invasive stages (Fleming, et al., AJCC (American Joint Committee on Cancer) Cancer Staging Manuel, 5th edition. Philadelphia: Lippincott-Raven, 1997). The treatment is usually by transurethral resection of bladder tumor (TURBT) followed by intravesical instillation of Bacillus Calmette-Guerin (BCG) or mitomycin C to reduce recurrence. Despite this treatment, 20-80% of patients will recur and 25% will have disease progression (Herr, et al., *J Clin Oncol*, (1995) 13: 1404-1408; Herr, et al., *J Urol*, (1989) 141: 22-29; and Cookson, et al., *J Urol*, (1997) 158: 62-67). All these patients require long-term follow-up with urine cytology and cystoscopy. The sensitivity of urine cytology ranges between 29-74%, with the overall sensitivity of approximately 35% (Eissa, et al., *Curr Opin Obstet Gynecol*, (2003) 15: 395-403; van Rhijn, et al., *Eur Urol*, (2005) 47: 736-748; and Lotan, et al., *Urology*, (2003) 61: 109-118). Cystoscopy is intrusive, uncomfortable and costly. Because of the long-term survival and the need for lifelong monitoring, the cost per case for bladder cancer is the highest among all cancer types, ranging from $96,000-$187,000 (2001 values) per case (Riley, et al., *Med Care*, (1995) 33: 828-841; Botteman, et al., *Pharmacoeconomics*, (2003) 21: 1315-1330).

The present invention is based, in part, on the use of combinatorial chemistry technology to develop bladder cancer-specific ligands for imaging and targeted therapy during the diagnosis, treatment and follow-up of bladder cancer. One-bead one-compound combinatorial peptide library technology (OBOC) (Lam, et al., *Nature*, (1991) 354: 82-84, 1991; and Lam, et al., *Chem Rev*, (1997) 97: 411-448) was used to identify bladder cancer specific ligands. When a "split-mix" synthesis method is performed to construct the combinatorial library, random libraries of millions of beads (90 μm in diameter) are generated. Each bead bears up to $10^{13}$ copies of ligands with the same amino acid sequences. At each round of screening, millions of library beads (ligands) can be screened in parallel for specific targets (receptor, antibody, enzyme, virus and whole cell, etc). Positive beads that bear peptides specific for the targets can be identified using an enzyme-linked colorimetric assay similar to the western blot, or by the evidence of cell attachment on the bead surface (Songyang, et al., *J Biol Chem*, (1995) 270: 14863-14866; and Liu, et al., *J Am Chem Soc*, (2002) 124: 7678-7680). Unnatural amino acids, D-amino acids or even non-peptide moieties can be incorporated in the library to make the molecules resistant to proteolysis and increase the binding affinity. The ligand leads identified through screening of OBOC libraries can be further optimized to generate cancer-specific ligands with high affinity and specificity (Peng, et al., *Nat Chem Biol*, (2006) 2: 381-389).

BRIEF SUMMARY OF THE INVENTION

The present invention provides peptides that selectively bind to bladder cancer tissue and bind minimally to or do not bind to normal bladder tissue or non-bladder tissue. Accordingly, in one aspect, the invention provides a peptide comprising the amino acid sequence $X_1DGRX_5GF$ (SEQ ID NO:18), wherein $X_1$ and $X_5$ are any amino acid, wherein the peptide is no longer than 10 amino acids in length and binds to bladder cancer cells. In some embodiments, the peptide is no longer than 9 amino acids in length. In some embodiments, the peptide is no longer than 8 amino acids in length. In some embodiments, the peptide is no longer than 7 amino acids in length.

In some embodiments, the peptide does not bind to normal cells, including normal bladder cells.

In a related embodiment, the invention provides a fusion protein comprising the amino acid sequence $X_1DGRX_5GF$ (SEQ ID NO: 18), wherein $X_1$ and $X_5$ are any amino acid and a second polypeptide (that is heterologous to the peptide). In some embodiments, the second polypeptide is the Fc portion of an immunoglobulin, for example, an IgG. In some embodiments, the second polypeptide is the Fc region of a human IgG1, IgG2, IgG3 and IgG4 isotype. In some embodiments, the second polypeptide is a cytotoxin.

In a related embodiment, the invention provides a polypeptide comprising the amino acid sequence $X_1DGRX_5GF$ (SEQ ID NO:18), wherein $X_1$ and $X_5$ are any amino acid, wherein the polypeptide is no longer than 300 amino acids in length, for example, no longer than 250, 200, 150, 100, 75, 50 or 25 amino acids in length, and binds to bladder cancer cells.

In a related embodiment, the invention provides a polypeptide or peptide comprising the amino acid sequence $X_1DGRX_5GF$ (SEQ ID NO: 1), wherein:

i) one or more of the amino acid residues are D-amino acids;

ii) the polypeptide or peptide comprises protecting groups at one or both of the N-terminus or the C-terminus;

iii) the polypeptide or peptide is fully or partially retro-inverso;

iv) the polypeptide or peptide comprises 2 or more repeats, for example, 3, 4, 5, 6 or more repeats, of the amino acid sequence $X_1DGRX_5GF$ (SEQ ID NO: 1);

v) the polypeptide or peptide is circularized;

vi) one or more of the amino acid residues are attached to a peptoid backbone;

vii) one or more of the amino acid residues are β amino acid residues; or
viii) the polypeptide or peptide is stabilized with a hydrocarbon staple.

In some embodiments, $X_1$ is Gln, Gly or Ala (SEQ ID NO: 19). In some embodiments, $X_5$ is Met, Lys, Gly, Ala or Gly-Gly (SEQ ID NO:3). In some embodiments, $X_1$ is Gln, Gly or Ala and $X_5$ is Met, Lys, Gly, Ala or Gly-Gly (SEQ ID NO:4).

In some embodiments, the peptide has the amino acid sequence QDGRMGF (SEQ ID NO:5). In some embodiments, the peptide has the amino acid sequence QDGRKGF (SEQ ID NO:6). In some embodiments, the peptide has the amino acid sequence QDGRK$_G$GF (SEQ ID NO:7), wherein K$_G$ refers to a lysine residue with a glycine residue attached to its side chain. These peptides optionally may be flanked at the N-terminus and/or the C-terminus with a D-cysteine residue, and optionally may be circularized.

In some embodiments, the peptide does not bind to normal bladder tissue.

In some embodiments, the peptide binds to integrin α5β3. In some embodiments, the peptide binds to integrin α5β5.

In some embodiments, the peptide further comprises from 1 to 5 flanking amino acid residues at the amino and/or carboxyl ends, for example, 1, 2, 3, 4 or 5 amino acid residues at the amino and/or carboxyl ends. In some embodiments, the peptide further comprises from 1 to 5 flanking amino acid residues at the amino and/or carboxyl ends (SEQ ID NO:8). In some embodiments, the peptide further comprises 2 flanking amino acid residues at the amino and/or carboxyl ends (SEQ ID NO:9). In some embodiments, the peptide has the amino acid sequence cX$_1$DGRX$_5$GFc (SEQ ID NO:20), wherein $X_1$ and $X_5$ are any amino acid, and c is D-cysteine. In some embodiments, the peptide is circularized.

In some embodiments, the bladder cancer-specific peptide (or repeats thereof) can be embedded within or located within a longer polypeptide sequence, for example, a fusion sequence or another non-naturally occurring polypeptide sequence. In some embodiments, the peptide is linked (e.g., via chemical linkage or fusion) to one or more additional polypeptides, e.g., at the amino and/or carboxyl ends. In some embodiments, the peptide is linked (e.g., via chemical linkage or fusion) to a therapeutic moiety or moieties, or a detectable label.

In some embodiments, the peptide is linked to a therapeutic moiety, e.g., to a cytotoxin, an anticancer agent, a radioisotope, or a Fc portion of an immunoglobulin ("Ig"), for example, an IgG. In some embodiments, the peptide is linked to the Fc region of a human IgG1, IgG2, IgG3 and IgG4 isotype. In some embodiments, the anticancer agent is encapsulated in a liposome. In some embodiments, the peptide is linked to a detectable label, e.g., an imaging label, a bead, a dye, a fluorophore, a chemiluminescent moiety, a magnetic particle (e.g., an iron oxide particle), a metal particle (e.g., a gold particle), a radioisotope (e.g., $^3$H, $^{32}$P, $^{125}$I, $^{123}$I, $^{11}$C, $^{13}$N, $^{15}$O, $^{18}$F, $^{82}$Rb, technetium-99m (Tc-99m), thallium-201).

In a related aspect, the invention provides compositions comprising a bladder cancer-specific polypeptide or peptide ligand, as described herein, and a pharmaceutically acceptable carrier. In some embodiments, the bladder cancer-specific peptides are formulated as a nanoparticle.

In a further aspect, the invention provides methods of detecting the presence of bladder cancer comprising contacting bladder cells or bladder tissue (or a tissue suspected of comprising bladder cancer metastasis) with a bladder cancer-specific peptide of the invention, and determining the binding of the peptide to the cells or tissue, wherein detecting binding of the peptide to the cells or tissue is indicative of bladder cancer, or the presence of bladder cancer metastasis. Embodiments of the bladder cancer-specific peptide are as described herein.

In a related aspect, the invention provides methods of detecting the presence of bladder cancer comprising contacting bladder cells in a urine sample with a bladder cancer-specific polypeptide or peptide ligand, as described herein, linked to a detectable label, and determining the binding of the peptide to the bladder cells, wherein detecting binding of the peptide to the bladder cells is indicative of bladder cancer, or the presence of bladder cancer metastasis. In some embodiments, the methods further comprise concentrating the bladder cells in the urine sample. In some embodiments, the bladder cancer-specific peptide is conjugated to a labeled bead. For example, the bead may be labeled with a fluorescent label, a chemiluminescent label or a quantum dot label. Further embodiments of the bladder cancer-specific peptide are as described herein.

In some embodiments, the signal for binding of the bladder cancer-specific peptide is detectable, indicating the presence of bladder cancer. In some embodiments, the signal for binding of the bladder cancer-specific peptide is not detectable, indicating the absence of bladder cancer. In some embodiments, the signal for binding of the bladder cancer-specific peptide is above a threshold level, indicating the presence of bladder cancer. In some embodiments, the signal for binding of the bladder cancer-specific peptide is below a threshold level, indicating the absence of bladder cancer. In some embodiments, the signal for binding of the bladder cancer-specific peptide is greater than the signal for binding of the bladder cancer-specific peptide to a normal control tissue (e.g., bladder cell or bladder tissue), indicating the presence of bladder cancer. In some embodiments, the signal for binding of the bladder cancer-specific peptide is about equivalent to or less than the signal for binding of the bladder cancer-specific peptide to a normal control tissue (e.g., bladder cell or bladder tissue), indicating the absence of bladder cancer.

In another aspect, the invention provides methods of inhibiting, reducing or preventing the growth of a bladder cancer cell in a subject in need thereof, comprising contacting the bladder cancer cell or bladder tissue (or a tissue comprising bladder cancer metastasis) with a bladder cancer-specific polypeptide or peptide, as described herein, linked to a therapeutic moiety, wherein the peptide binds to bladder cancer cells and the therapeutic moiety inhibits, reduces or prevents the growth of the bladder cancer cells or kills bladder cancer cells. Embodiments of the bladder cancer-specific peptide are as described herein.

The bladder cancer-specific peptide ligands are also therapeutic in themselves in that they can be used to block, inhibit, reduce or prevent the growth, migration and metastasis of bladder cancer cells. Accordingly, in a related aspect, the invention provides methods of inhibiting or preventing the growth of a bladder cancer cell in a subject in need thereof, comprising contacting the bladder cancer cell or bladder tissue (or a tissue comprising bladder cancer metastasis) with a bladder cancer-specific polypeptide or peptide, as described herein, wherein the peptide binds to bladder cancer cells and blocks, inhibits, reduces or prevents the growth, migration and metastasis of the bladder cancer cells. Embodiments of the bladder cancer-specific peptide are as described herein.

In another aspect, the invention provides methods for the in situ detection of bladder cancer in a tissue, comprising contacting the tissue with a bladder cancer-specific polypeptide or peptide ligand, as described herein, wherein the peptide binds to bladder cancer cells in the tissue, thereby detecting the bladder cancer cells in situ in the tissue. The tissue can be within the subject suspected of having or known to have bladder cancer. The tissue can be bladder tissue, or another tissue, e.g., suspected of containing bladder cancer metastasis. This can be done, e.g., for the purposes of imaging or facilitating the resection of tumor. In some embodiments, the methods further comprise capturing and/or recording the image of the bladder cancer cells within the tissue, e.g., based on detecting the binding of the bladder cancer-specific peptide ligands. In some embodiments, the methods further comprise removing, resecting or excising the bladder cancer cells from the tissue, e.g., based on detecting the binding of the bladder cancer-specific peptide ligands.

In some embodiments, the bladder cancer cell or bladder tissue is in vitro. For example, in some embodiments, the peptide is contacted with a bladder cell in a urine sample.

In some embodiments, the bladder cancer cell or bladder tissue is in vivo, i.e., in a subject.

In some embodiments, the subject is a mammal, for example, human, non-human primate or canine.

In some embodiments, the peptide is administered to the subject intravenously, intratumorally or intraurethrally.

The invention further provides kits comprising a bladder cancer-specific ligand, as described herein.

Definitions

A "toxic moiety" is the portion of a chimeric molecule which renders the chimeric molecule cytotoxic to cells of interest.

The term "effector moiety" or "therapeutic moiety" refers to the portion of a chimeric molecule intended to have an effect on a cell targeted by the targeting moiety (i.e., peptide ligand PLZ4) or to identify the presence of the immunoconjugate.

The term "chimeric molecule" includes reference to a covalent linkage of an effector molecule to a bladder cancer specific peptide of the invention.

The term "cytotoxin" typically includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain 1a of PE or the B chain of DT) and replacing it with a different targeting moiety, such as an antibody.

The term "contacting" includes reference to placement in direct physical association.

As used herein, "polypeptide", "peptide" and "protein" are used interchangeably and include reference to a polymer of amino acid residues. As used herein, the term "peptide" is used in its broadest sense to refer to conventional peptides (i.e. short polypeptides containing L or D-amino acids), as well as peptide equivalents, peptide analogs and peptidomimetics that retain the desired functional activity. Peptide equivalents can differ from conventional peptides by the replacement of one or more amino acids with related organic acids (such as PABA), amino acids or the like, or the substitution or modification of side chains or functional groups. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The terms "peptide equivalents", "peptide analogs", "peptide mimetics", and "peptidomimetics" are used interchangeably unless specified otherwise. Peptide analogs are commonly used in the pharmaceutical industry as non-peptide drugs with properties analogous to those of the template peptides. (Fauchere, J. (1986) Adv. Drug Res. 15: 29; Veber and Freidinger (1985) TINS p. 392; and Evans et al. (1987) J. Med. Chem 30: 1229). Peptide analogs are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)$ $CH_2$—, and —$CH_2SO$—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., Trends Pharm Sci (1980) pp. 463-468 (general review); Hudson, D. et al., Int J Pept Prot Res (1979) 14:177-185 (—$CH_2NH$—, $CH_2CH_2$—); Spatola, A. F. et al., Life Sci (1986) 38:1243-1249 (—$CH_2S$); Hann, M. M., J Chem Soc Perkin Trans I (1982) 307-314 (—CH═CH—, cis and trans); Almquist, R. G. et al., J Med Chem (1980) 23:1392-1398 (—$COCH_2$—); Jennings-White, C. et al., Tetrahedron Lett (1982) 23:2533 (—$COCH_2$—); Szelke, M. et al., European Appln. EP 45665 (1982) CA: 97:39405 (1982) (—$CH(OH)CH_2$—); Holladay, M. W. et al., Tetrahedron Lett (1983) 24:4401-4404 (—$C(OH)CH_2$—); and Hruby, V. J., Life Sci (1982) 31:189-199 (—$CH_2$—S—). Portions or all of the peptide backbone can also be replaced by conformationally constrained cyclic alkyl or aryl substituents to restrict mobility of the functional amino acid sidechains specified herein as described in the following references: 1. Bondinell et al. Design of a potent and orally active nonpeptide platelet fibrinogen receptor (GPIIb/IIIa) antagonist. Bioorg Med Chem 2:897 (1994). 2. Keenan et al. Discovery of potent nonpeptide vitronectin receptor (alpha v beta 3) antagonists. J Med Chem 40:2289 (1997). 3. Samanen et al. Potent, selective, orally active 3-oxo-1,4-benzodiazepine GPIIb/IIIa integrin antagonists. J Med Chem 39:4867 (1996).

The peptides of this invention may be produced by recognized methods, such as recombinant and synthetic methods that are well known in the art. Recombinant techniques are generally described in Sambrook, et al., Molecular Cloning: A Laboratory Manual, (3rd ed.) Vols. 1-3, Cold Spring Harbor Laboratory, (2001). Techniques for the synthesis of peptides are well known and include those described in Merrifield, J. Amer. Chem. Soc. 85:2149-2456 (1963), Atherton, et al., Solid Phase Peptide Synthesis: A Practical Approach, IRL Press (1989), and Merrifield, Science 232:341-347 (1986).

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S-Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *Proteins: Structures and Molecular Properties*, W. H. Freeman and Company, New York (2nd Ed., 1992).

The terms "substantially similar" in the context of a peptide indicates that a peptide comprises a sequence with at least 95%, 96%, 97%, 98%, 99% sequence identity to the reference sequence over a comparison window of 7-10 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, the term "retro-inverso peptide" refers to a peptide that typically comprises the same amino acid sequence as a peptide having L-amino acids, but whose sequence is comprised partially or entirely of D-amino acids, thus having a reversed stereochemistry from a peptide which is synthesized using L-amino acids. By constructing a peptide using the D-amino acids in inverse order (i.e. the sequences are denoted from left to right, from C-terminal to N-terminal amino acid as opposed to from N-terminal to C-terminal as written or denoted in the case of L-amino acids; see infra), one obtains a retro-inverso peptide that restores the same stereochemistry for the side chains as the parent L-amino acid peptide. Use of retro-inverso peptide sequences minimizes enzymatic degradation and, therefore, extends biological half-life of the peptide moiety. Also, these sequences may favorably alter potential immunogenic properties of the analogous conjugates prepared from normal L-amino acid sequences. The retro-inverso sequences (as free peptides or conjugates) are particularly useful in those applications that require or prefer orally active agents (due to resistance to enzymolysis). For the purposes of the present invention, retro-inverso peptides are denoted by "ri", and are written, from left to right, from the C-terminal to the N-terminal amino acid, e.g. the opposite of typical L-peptide notation. In one embodiment, the retro-inverso peptide of the present invention incorporates all D isomer amino acids. When the retro-inverso peptide incorporate all D isomer amino acids, it is termed a "D-reverse peptide".

The terms "substantially pure," or "isolated" when used to describe peptides, refers to a peptide separated from proteins or other contaminants with which they are naturally associated or with which they are associated during synthesis. In one embodiment, a peptide or polypeptide makes up at least 50% of the total polypeptide content of the composition containing the peptide, and in one embodiment, at least 60%, in one embodiment, at least 75%, in one embodiment at least 90%, and in one embodiment, at least 95% of the total polypeptide content.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of a ligand (here, a bladder cancer-specific peptide ligand), in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive ligands bind antigen, they may do so with low affinity. On the other hand, specific binding results in a much stronger association between the ligand and cells bearing the antigen than between the bound ligand and cells lacking the antigen. Specific binding typically results in greater than 2-fold, preferably greater than 5-fold, more preferably greater than 10-fold and most preferably greater than 100-fold increase in amount of bound ligand (per unit time) to a cell or tissue bearing the target antigen as compared to a cell or tissue lacking the target antigen. Specific binding to a protein under such conditions requires a ligand that is selected for its specificity for a particular protein. A variety of assay formats are appropriate for selecting ligands specifically immunoreactive with a particular protein. For example, solid-phase assays are routinely used to ligands that specifically bind to antigens. See Harlow & Lane, ANTIBODIES, A LABORATORY MANUAL, Cold Spring Harbor Publications, New York (1988), for a description of assay formats and conditions that can be used to determine specific binding reactivity.

The term "threshold level" refers to a predetermined level of signal (here, of binding of a bladder cancer-specific peptide to a bladder cell or to bladder tissue), above which indicates binding and a positive diagnosis of bladder cancer, and below which indicates non-binding and a negative diagnosis of bladder cancer. The level of signal can be based on determinations from a population of individuals.

The terms "patient," "subject," "individual" interchangeably refer to a mammal, for example, a human or a non-human primate, a domesticated mammal (e.g., a canine or feline), an agricultural mammal (e.g., a bovine, porcine, ovine, equine), a laboratory mammal (a mouse, rat, hamster, rabbit).

The term "co-administer" refers to the simultaneous presence of two active agents in the blood of an individual. Active agents that are co-administered can be concurrently or sequentially delivered.

The terms "effective amount" or "amount effective to" or "therapeutically effective amount" includes reference to a dosage of a therapeutic agent sufficient to produce a desired result, such as inhibiting, reducing or preventing bladder cancer cell growth or tumor growth; promoting bladder tumor reduction or elimination; or blocking, reducing, inhibiting or preventing bladder cancer growth, migration or metastasis. The term "effective amount" as used in relation to pharmaceutical compositions, typically refers to the amount of the active ingredient, e.g. the peptides of the invention, which are required to achieve the desired goal. For example, in therapeutic applications, an effective amount will be the amount required to be administered to a patient to result in treatment of the particular disorder for which treatment is sought (e.g., bladder cancer). The term "treatment of a disorder" denotes the reduction or elimination of symptoms of a particular disorder. Effective amounts will typically vary depending upon the nature of the disorder, the peptides used, the mode of administration, and the size and health of the patient. In one embodiment, the effective amount of the peptides of the invention ranges from 1 µg to 1 g of peptide for a 70 kg patient, and in one embodiment, from 1 µg to 10 mg. In one embodiment, the concentration of peptide (or peptide analog) administered ranges from 0.1 µM to 10 mM, and in one embodiment, from 5 µM to 1 mM, in one embodiment, from 5 µM to 100 and in one embodiment from 5 µM to 40 µM.

As used herein, the terms "treating" and "treatment" refer to delaying the onset of, retarding or reversing the progress of, or alleviating or preventing either the disease or condition to which the term applies (e.g., bladder cancer), or one or more symptoms of such disease or condition.

The terms "inhibiting," "reducing," "decreasing" with respect to tumor or cancer growth or progression refers to inhibiting the growth, spread, metastasis of a tumor or cancer in a subject by a measurable amount using any method known in the art. The growth, progression or spread of a tumor or cancer is inhibited, reduced or decreased if the tumor burden is at least about 10%, 20%, 30%, 50%, 80%, or 100% reduced in comparison to the tumor burden prior to the co-administration of a peptide of the present invention, e.g., as part of a chimeric molecule. In some embodiments, the growth, progression or spread of a tumor or cancer is inhibited, reduced or decreased by at least about 1-fold, 2-fold, 3-fold, 4-fold, or more in comparison to the tumor burden prior to administration of the peptide.

BRIEF DESCRIPTION OF THE DRAWINGS

FIG. 1. Whole cell binding assay to screen ligands binding to bladder cancer cells. In this assay, single cell suspension was incubated with OBOC libraries. If the peptides on bead surface can bind to cell surface molecules, those beads are covered will cells. In the middle of each panel, one positive bead was covered with bladder cancer cells, suggesting the peptide on this bead could bind to bladder cancer cells in test while peptides on other beads could not bind to the cells in test. The incubation time, cell and library types are shown next to each panel. The average bead diameter is around 90 µm.

FIG. 2A-H. PLZ4 can bind to bladder tumor cells, but not to normal urothelial cells or other confounding cells. PLZ4 bound to three bladder TCC cells: 5637 (A), T24 (B) and TCCSUP (C), but not to normal urothelial cells (D). The heterogeneity of cell size of normal urothelial cells in Panel D suggests the presence of cells from basal (small cells) to suprabasal layers of urothelium. No binding of PLZ4 was observed under a microscopy with whole blood cells (E), PBMC (F), normal fibroblasts (G) and cells from a patient who received active treatment with BCG intravesical therapy (H). The bead diameter is around 90 µm.

FIG. 5A-F. In vivo NIRF imaging of tumor-bearing mice. Mouse tumor xenografts were established with the primary bladder cancer tissue from patients who underwent cystectomy for resection of bladder cancer. PLZ4-Cy5.5 (7 nmol) was injected through tail vein. Panels A-D. Near infrared imagings. Panel A. mouse received SA-CY5.5 alone. Panel B. Mouse received PLZ4-CY5.5 conjugate. The red arrow points to the tumor xenograft with strong uptake of CY5.5. Panel C. Ex vivo imaging of xenograft and organs from the mouse that received SA-Cy 5.5, showing uptake in kidneys and weak autofluorescence in tumor xenograft. Panel D. Ex vivo imaging of xenograft and organs from mouse receiving PLZ4-Cy5.5, showing fluorescence in tumor xenograft and kidneys. Panel E and F. Light imaging of panels C and D, respectively. Fluorescence intensity is shown in arbitrary units at the bottom.

DETAILED DESCRIPTION

1. Introduction

Figures 3A, 3B, 3C, 3D, 3E:
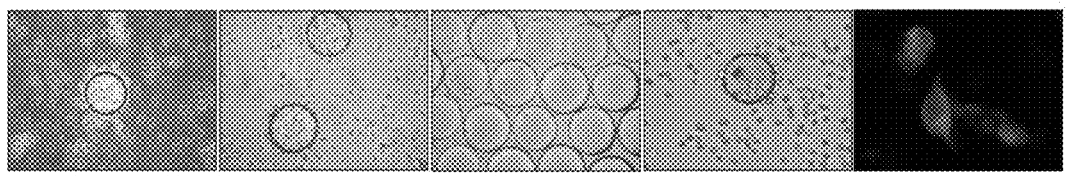
FIGS. 3A-E. Binding of PLZ4 to human and canine bladder cancer cells. Single cells suspension from freshly resected human bladder cancer specimens were incubated with beads coated with PLZ4. A significant binding was observed with cells from human patients (A and B). Cells from the normal bladder of the same patient as in Panel B did not bind to beads coated with PLZ4 (C). Cells in Panel C were washed away to decrease overlap of cells with beads. PLZ4-coated beads could bind to bladder cancer cell 5637 cells after 4 hours of incubation in urine with pH 6.0 (D). PLZ4-FITC conjugate could bind to canine bladder cancer cells (E). The bead diameter is 90 µm.

Most bladder transitional cell cancer cases are diagnosed at non-invasive stages. Non-invasive bladder cancer is ideal for targeted therapy because it is easily accessible through intravesical instillation, relatively isolated from the rest of the human body and has only a few confounding cells. High throughput screening of one-bead one-compound combinatorial peptide libraries was performed and the illustrative bladder cancer-specific ligand PLZ4 (the amino acid sequence: cQDGRMGFc; SEQ ID NO:12) was identified. PLZ4 can selectively bind to bladder cancer cell lines and primary bladder cancer cells from patients, but not to normal urothelial cells, normal cell mixture from bladder specimens, fibroblasts and blood cells. It can bind to all five canine bladder cancer cell lines tested. This ligand can bind to tumor cells treated with urine at pH 6.0, but not to cells collected from the urine of four patients actively treated with intravesical Bacillus Calmette-Guerin therapy. Intravenous injection of PLZ4 linked to near-infrared dye Cy5.5 showed fluorescent uptake in mouse xenografts developed from excised human primary bladder cancer specimens. Thus, this ligand can be used for imaging detection and targeted therapy of bladder cancer. PLZ4 binds to K562 cells expressing αvβ3 integrin, but not other integrins. Using alanine walk and a rainbow bead coding system, the amino acids important for cell binding were determined. Structural analysis indicated that there are two domains required for cell binding. The bladder cancer-specific peptide ligands described herein, including PLZ4 can be used, e.g., for imaging detection for diagnosis and follow-up/surveillance, and targeted therapy of bladder cancer.

The present invention is based, in part, on bladder cancer-specific ligands, illustrated by peptide PLZ4 (cQDGRMGFc (SEQ ID NO:12), that in vitro specifically bound to human bladder transitional cell carcinoma (TCC) cell lines and bladder cancer cells from clinical patients, and in vivo, concentrated in mice at tumor xenografts developed from patient cystectomy specimens (Zhang, et al, *Urologic Oncology: Seminars and Original Investigations* (2010) In press). Moreover, preclinical studies show the potential of the bladder cancer-specific ligands for diagnostic and targeted therapeutic purposes in humans and other mammals.

Because the TCC-bearing dog serves as a spontaneous, outbred, immune-competent, large animal model for TCC in the human, and because bladder TCC is the most common urinary cancer in dogs (87% of all cases) (Fink, et al., *Cancer Res* (1997) 57:1841-1845), it was determined that that bladder cancer-specific ligands could bind to canine bladder cancer. Because binding of the bladder cancer-specific ligands occurred, dogs with naturally-occurring canine bladder cancer are a relevant model for use in preclinical studies for human therapy and diagnosis (Deborah, et al., *Urologic Oncology* (2000) 5:47-59.; Dhawan, et al., *Urologic Oncology* (2009) 27:284-292), as the bladder tumors in canines possess similar histopathologic appearance, molecular features, biological behavior, and response to chemotherapy as do muscle-invasive bladder TCC in humans (Patrick, et al., *J Comp Pathol* (2006) 135:190-199. and Mutsaers, et al., *J Vet Intern Med* (2003) 17:136-144). The present bladder-cancer-specific ligands find use for the diagnostic and therapeutic purposes in the management of bladder cancer.

2. Bladder Cancer-Specific Peptide Ligands

The present invention provides peptide ligands that preferentially and specifically bind to bladder cancer tissue, and that bind minimally to or do not bind to normal bladder tissue or to non-bladder tissue. Generally, the bladder cancer-specific peptide ligands comprise the amino acid sequence $X_1DGRX_5GF$, wherein $X_1$ and $X_5$ are any amino acid other than cysteine (e.g., A, D, E, F, G, H, I, K, L, M, N, P, Q, R, S, T, V, W, Y) (SEQ ID NO:1). The peptides are generally about 7 to 10 or 7 to 9 amino acids in length. In some embodiments, the peptide is no longer than 10 amino acids in length. In some embodiments, the peptide is no longer than 9 amino acids in length. In some embodiments, the peptide is no longer than 8 amino acids in length. In some embodiments, the peptide is no longer than 7 amino acids in length.

In various embodiments, the polypeptide comprises the amino acid sequence $X_1DGRX_5GF$ (SEQ ID NO:18), wherein $X_1$ and $X_5$ are any amino acid, wherein the polypeptide is no longer than 300 amino acids in length, for example, no longer than 250, 200, 150, 100, 75, 50 or 25 amino acids in length, and binds to bladder cancer cells.

In various embodiments, the polypeptide or peptide comprises the amino acid sequence $X_1DGRX_5GF$ (SEQ ID NO:1), wherein:

i) one or more, for example, 2, 3, 4, 5, 6, 7, 8, 9, 10 or all, of the amino acid residues are D-amino acids;

ii) the polypeptide or peptide comprises protecting groups at one or both of the N-terminus or the C-terminus (for example, the N-terminus can be acetylated and the C-terminus can have an amino group);

iii) the polypeptide or peptide is fully or partially retro-inverso;

iv) the polypeptide or peptide comprises 2 or more repeats, for example, 3, 4, 5, 6 or more repeats, of bladder cancer-specific peptide the amino acid sequence, e.g., $X_1DGRX_5GF$ (SEQ ID NO:1);

v) the polypeptide or peptide is circularized;

vi) one or more of the amino acid residues are attached to a peptoid backbone;

vii) one or more of the amino acid residues are β amino acid residues; or viii) the polypeptide or peptide is stabilized with a hydrocarbon staple.

In some embodiments, the peptides may have from 1 to 5 flanking L- or D-cysteine residues at the N-terminal and C-terminal ends, e.g., to allow for circularization and/or conjugation of the peptide. For example, the peptide ligands can comprise the amino acid sequence $CX_1DGRX_5GFC$ (SEQ ID NO:17) or $cX_1DGRX_5GFc$ (SEQ ID NO:10), wherein $X_1$ and $X_5$ are any amino acid other than cysteine (e.g., A, D, E, F, G, H, I, K, L, M, N, P, Q, R, S, T, V, W, Y) and c is D-cysteine. In various embodiments, the peptide ligands are circularized.

In some embodiments, $X_1$ is Q, G or A (SEQ ID NO:2) and $X_5$ is any amino acid other than cysteine (e.g., A, D, E, F, G, H, I, K, L, M, N, P, Q, R, S, T, V, W, Y). In some embodiments, $X_1$ is any amino acid other than cysteine (e.g., A, D, E, F, G, H, I, K, L, M, N, P, Q, R, S, T, V, W, Y) and $X_5$ is M, K, G, A or GG (SEQ ID NO:21). In some embodiments, $X_1$ is Q, G or A and $X_5$ is M, K, G, A or GG (SEQ ID NO:4).

In some embodiments, the bladder cancer-specific peptide ligand has the amino acid sequence QDGRMGF (SEQ ID NO:5). In some embodiments, the peptide has the amino acid sequence QDGRKGF (SEQ ID NO:6). In some embodiments, the peptide has the amino acid sequence QDGRK$_G$GF (SEQ ID NO:7), wherein K$_G$ refers to a lysine residue with a glycine residue attached to its side chain. Additional amino acid residues can be added to either the amino and/or carboxyl terminus, for example from 1-5 amino acid residues, for example, 1, 2, 3, 4 or 5 amino acid residues. Cysteine residues can be added to the amino and carboxy terminus to allow for circularization.

In some embodiments, the bladder cancer-specific peptide ligand has the amino acid sequence $X_{(1-5)}X_6DGRX_7GFX_{(8-12)}$ (SEQ ID NO:22), wherein $X_{(1-5)}$ and $X_{(8-12)}$ are any amino acid (i.e., A, C, D, E, F, G, H, I, K, L, M, N, P, Q, R, S, T, V, W, Y); $X_6$ and $X_7$ are any amino acid other than cysteine (i.e., A, D, E, F, G, H, I, K, L, M, N, P, Q, R, S, T, V, W, Y). In some embodiments, the bladder cancer-specific peptide ligand has the amino acid sequence $X_1X_2X_3DGRX_4GFX_5X_6$ (SEQ ID NO:23), wherein $X_1$, $X_2$, $X_5$, $X_6$ are any amino acid (i.e., A, C, D, E, F, G, H, I, K, L, M, N, P, Q, R, S, T, V, W, Y); $X_3$ and $X_4$ are any amino acid other than cysteine (i.e., A, D, E, F, G, H, I, K, L, M, N, P, Q, R, S, T, V, W, Y). In some embodiments, the bladder cancer-specific peptide ligand has the amino acid sequence $cX_1DGRX_5GFc$ (SEQ ID NO:10), wherein $X_1$ is any amino acid other than cysteine (i.e., A, D, E, F, G, H, I, K, L, M, N, P, Q, R, S, T, V, W, Y); $X_5$ is any amino acid other than cysteine (i.e., A, D, E, F, G, H, I, K, L, M, N, P, Q, R, S, T, V, W, Y), and c is D-cysteine. In some embodiments, the bladder cancer-specific peptide ligand has the amino acid sequence cQDGRKGFc (SEQ ID NO:11), wherein c is D-cysteine. In some embodiments, the bladder cancer-specific peptide ligand has the amino acid sequence cQDGRMGFc (SEQ ID NO:12), wherein c is D-cysteine. In some embodiments, the bladder cancer-specific peptide ligand has the amino acid sequence cQDGRK$_{(G1-6)}$Fc (SEQ ID NO:13), wherein c is D-cysteine, wherein K$_{(G1-6)}$ refers to a lysine residue with one to six glycine residues attached to its side chain. In some embodiments, the bladder cancer-specific peptide ligand has the amino acid sequence CQDGRMGFC (SEQ ID NO:14). In some embodiments, the peptide is circularized.

One or more of the amino acids in the bladder cancer-specific peptides can be D-amino acids. In some embodiments, all amino acid residues in the peptide ligands are D-amino acids. In various embodiments, the peptide ligands are partial retro-inverso or full-retro-inverso.

Generally, the bladder cancer-specific peptides are substantially purified and/or isolated.

Additional amino acid residues or polypeptide sequences may optionally be linked (e.g., either via chemical linkage or fusion) to either the amino and/or carboxy termini of the peptide ligands. In some embodiments, the bladder cancer-specific peptide sequences described herein can be embedded within or located within a longer polypeptide sequence, for example, a fusion sequence or another non-naturally occurring polypeptide sequence. For example, in various embodiments, the peptides are linked to the Fc portion of an immunoglobulin (e.g., to promote antibody-dependent cellular cytotoxicity (ADCC) and/or complement-dependent cytotoxicity (CDC)) or to a cytotoxin. In some embodiments, the bladder cancer-specific peptide ligand is linked to the Fc region of an IgG antibody. In some embodiments, the bladder cancer-specific peptide ligand is linked to the Fc region of a human IgG1, IgG2, IgG3 and IgG4 isotype.

In some embodiments, the bladder cancer-specific peptide ligands are conjugated to a therapeutic agent. In some embodiments, the therapeutic agent is a neoplastic agent. Illustrative neoplastic agent include without limitation alkylating agents (cisplatin, carboplatin, and oxaliplatin); antimetabolites (purine or pyrimidine mimetics including for example azathioprine and mercaptopurine); plant alkaloids and terpenoids (vinca alkaloids and taxanes); vinca alkaloids (vincristine, vinblastine, vinorelbine, and vindesine); podophyllotoxin (including etoposide and teniposide); taxanes (paclitaxel, taxol and docetaxel); topoisomerase inhibitors (Type I inhibitors: camptothecins, irinotecan and topotecan; Type II Inhibitors: amsacrine, etoposide, etoposide phosphate, and teniposide); antineoplastics (dactinomycin, doxorubicin, epirubicin, fludarabine and bleomycin). Any chemotherapeutic agent being used to treat the cancer of interest can be conjugated to the bladder cancer-specific peptide ligands. In various embodiments, the antineoplastic agent is encapsulated in a liposome.

In some embodiments, the therapeutic agent is a cytotoxin. Illustrative cytotoxins that find use include abrin, ricin, *Pseudomonas* exotoxin (PE), diphtheria toxin (DT), botulinum toxin, or modified toxins thereof. Other cytotoxins also find use.

In various embodiments, the bladder cancer-specific peptide ligands are conjugated to a radioactive isotope, for example, $^{125}$, $^{32}$P, $^{14}$C, $^{3}$H, $^{35}$S, $^{123}$I, $^{11}$C, $^{13}$N, $^{15}$O, $^{18}$F, $^{82}$Rb, technetium-99m (Tc-99m) or thallium-201. In various embodiments, the bladder cancer-specific peptide ligands are conjugated to a magnetic particle, for example a magnetic bead or an iron oxide particle (e.g., for magnetic resonance imaging (MRI)).

3. Compositions Comprising Bladder Cancer-Specific Ligands

The bladder cancer-specific peptide ligands can be prepared as a variety of pharmaceutical formulations for administration to a patient, including liquid and solid form preparations.

Compositions comprising the bladder cancer-specific peptide ligands are useful for parenteral, topical, oral, or local administration, including by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the polypeptides and pharmaceutical compositions of this invention, when administered orally, must be protected from digestion. This is typically accomplished either by complexing the polypeptide with a composition to render it resistant to acidic and enzymatic hydrolysis or by packaging the protein in an appropriately resistant carrier such as a liposome. Means of protecting proteins from digestion are well known in the art.

Compositions comprising the bladder cancer-specific peptide ligands are particularly useful for parenteral administration, such as intravenous administration or administration into a body cavity or lumen of an organ (e.g., the bladder). The compositions for administration will commonly comprise a solution of the polypeptide comprising the polypeptide dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of polypeptide in these formulations can vary widely, and will be selected primarily based on fluid volumes, viscosities, body weight and the like in accordance with the particular mode of administration selected and the patient's needs.

Liquid form pharmaceutical preparations can include solutions, suspensions, and emulsions, for example, water or water/propylene glycol solutions. Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

In some embodiments, the bladder cancer-specific peptides are formulated as a nanoparticle. Peptide nanoparticles and methods for their preparation are known in the art and described, e.g., in U.S. Patent Publication No. 2006/0251726, U.S. Patent Publication No. 2004/0126900, U.S. Patent Publication No. 2005/0112089, U.S. Patent Publication No. 2010/0172943, U.S. Patent Publication No. 2010/0055189, U.S. Patent Publication No. 2009/0306335, U.S. Patent Publication No. 2009/0156480, and U.S. Patent Publication No. 2008/0213377, each of which is hereby incorporated herein by reference in its entirety for all purposes. Further nanoparticle formulations that find use are described, e.g., in Emerich and Thanos, *Curr Opin Mol Ther* (2008) 10(2):132-9; Kogan, et al., *Nanomedicine* (2007) 2(3):287-306; Zhang, et al., *Bioconjug Chem* (2008) 19(1): 145-152; Scarberry, et al., *J Am Chem Soc* (2008) 130(31): 10258-10262; and Fraysse-Ailhas, et al., *Eur Cells Materials* (2007) 14(Suppl. 3):115. As appropriate, amino acid sequences may be added to either or both the N-terminus and the C-terminus of the peptide ligands in order to allow assembly and formation of the peptide nanoparticle.

Also contemplated are solid form pharmaceutical formulations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical formulation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

In one embodiment, a pharmaceutical formulation is administered to a patient at a therapeutically effective dose to prevent, treat, or control a disease or malignant condition, such as cancer. The pharmaceutical composition or medicament is administered to a patient in an amount sufficient to elicit an effective therapeutic or diagnostic response in the patient. An effective therapeutic or diagnostic response is a response that at least partially arrests or slows the symptoms or complications of the disease or malignant condition. An amount adequate to accomplish this is defined as "therapeutically effective dose."

4. Methods of Treatment and/or Prevention a. Subjects Amenable to Treatment and/or Prevention The bladder cancer-specific peptide ligands described herein find use in the treatment and prevention of bladder cancer. Bladder cancer refers to any of several types of malignant growths of the urinary bladder. The most common type of bladder cancer begins in cells lining the inside of the bladder and is called transitional cell carcinoma (TCC) (sometimes called urothelial cell carcinoma (UCC)). Other types of bladder cancer include squamous cell carcinoma, adenocarcinoma, sarcoma and small cell carcinoma. In some embodiments, the subject has or is at risk of developing a bladder cancer, e.g., due to genetic, lifestyle or environmental risk factors. In some embodiments, the subject has or is at risk of developing a transitional cell carcinoma of the bladder tissue. In some embodiments, the subject has or is at risk of developing a bladder cancer that expresses or over-expresses integrin $\alpha5\beta3$ and/or integrin $\alpha5\beta5$.

The subject may be asymptomatic or exhibiting symptoms of bladder cancer. The subject may have a familial history of bladder cancer, e.g., a parent, grandparent or sibling who has been diagnosed with bladder cancer.

The bladder cancer-specific peptide ligands can be administered to a patient to effect the inhibition, reduction, retraction or prevention of proliferation or growth of a bladder tumor or bladder cancer cell. In the context of effecting treatment, the patient has a bladder cancer or a bladder tumor burden, and administration of the bladder cancer-specific peptide ligands can reverse, delay or inhibit progression of the disease. In the context of effecting prevention, the patient may be in remission, or may have undergone the removal of a primary tumor, and administration of the bladder cancer-specific peptide ligands can delay, reduce, inhibit or eliminate growth of metastasis.

b. Methods of Administering Polypeptides i. Routes of Administration

The bladder cancer-specific peptide ligands described herein can be formulated into pharmaceutical formulations for administration to a patient. Administration of the pharmaceutical formulations can be by a variety of methods. Methods can include systemic administration, wherein the polypeptide or composition of polypeptides is delivered to sites in the body, including the targeted site of pharmaceutical action, via the circulatory system. Systemic administration includes, but is not limited to, oral, intraurethral and parenteral (i.e., other than through the alimentary tract, such as intramuscular, intravenous, intra-arterial, transdermal and subcutaneous) administration. In other embodiments administration of the bladder cancer-specific peptide ligands is local, e.g., directly into the bladder or intratumorally.

ii. Dosing

The bladder cancer-specific peptide ligands can be administered for prophylactic and/or therapeutic treatments. In therapeutic applications, compositions comprising the bladder cancer-specific peptide ligands are administered to a patient suffering from a bladder cancer in an amount sufficient to cure or at least partially arrest the disease and its complications. An amount adequate to accomplish this is defined as a "therapeutically effective dose." Amounts effective for this use will depend upon the severity of the disease and the general state of the patient's health, and clinical studies are often done to determine the best dose for a given cancer type. An effective amount of the compound is that which provides either subjective relief of a symptom(s) or an objectively identifiable improvement as noted by the clinician or other qualified observer.

In prophylactic applications, compositions containing the bladder cancer-specific peptide ligands are administered to a patient not already in a disease state to prevent the onset of disease. Such an amount is defined to be a "prophylactically effective dose." In this use, the precise amounts again depend upon the patient's state of health.

Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics,* 11th Edition, 2006, supra; in a Physicians' Desk Reference (PDR), 64$^{th}$ Edition, 2010; in *Remington: The Science and Practice of Pharmacy,* 21$^{st}$ Ed., 2006, supra; and in *Martindale: The Complete Drug Reference,* Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

Exemplary doses of the pharmaceutical formulations described herein, include milligram or microgram amounts of the bladder cancer-specific peptide ligands per kilogram of subject or sample weight (e.g., about 1 microgram per-kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of the bladder cancer-specific peptide ligands depend upon the potency of the composition with respect to the desired effect to be achieved. When the bladder cancer-specific peptide ligands are to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

The appropriate dosage of the polypeptides of the present invention will vary according to several factors, including the chosen route of administration, the formulation of the composition, patient response, the severity of the condition, the subject's weight, and the judgment of the prescribing physician. The dosage can be increased or decreased over time, as required by an individual patient. Usually, a patient initially is given a low dose, which is then increased to an efficacious dosage tolerable to the patient.

The dosage of bladder cancer-specific peptide ligands administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular compound in a particular subject. A unit dosage for administration to a mammal of about 50 to 70 kg may contain between about 5 and 500 mg of the active ingredient. Typically, a dosage of the bladder cancer-specific peptide ligands, is a dosage that is sufficient to achieve the desired effect.

Optimum dosages, toxicity, and therapeutic efficacy of compositions can further vary depending on the relative potency of individual compositions and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compositions that exhibit large therapeutic indices are preferred. While compositions that exhibit toxic side effects can be used, care should be taken to design a delivery system that targets such compositions to the site of affected tissue to minimize potential damage to normal cells and, thereby, reduce side effects.

The data obtained from, for example, animal studies (e.g., rodents and monkeys) can be used to formulate a dosage range for use in humans. The dosage of polypeptides of the present invention lies preferably within a range of circulating concentrations that include the $ED_{50}$ with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a polypeptide or composition, is from about 1 ng/kg to 100 mg/kg for a typical subject.

A typical polypeptide composition of the present invention for intravenous administration would be about 0.1 to 10 mg/kg per patient per day. Dosages from 0.1 up to about 100 mg/kg per patient per day may be used. Actual methods for preparing administrable compositions will be known or apparent to those skilled in the art and are described in more detail in such publications as *Remington: The Science and Practice of Pharmacy*, 21$^{st}$ Ed., 2006, Lippincott Williams & Wilkins.

In one embodiment of the present invention, a pharmaceutical formulation of the present invention is administered, e.g., in a daily dose in the range from about 1 mg of compound per kg of subject weight (1 mg/kg) to about 1 g/kg. In another embodiment, the dose is a dose in the range of about 5 mg/kg to about 500 mg/kg. In yet another embodiment, the dose is about 10 mg/kg to about 250 mg/kg. In another embodiment, the dose is about 25 mg/kg to about 150 mg/kg. A preferred dose is about 10 mg/kg.

Exemplary doses of the pharmaceutical formulations can include 100-500 mg daily doses as needed. Pharmaceutical formulations can be administered at a concentration of about 25 mg/mL to about 50 mg/mL. Exemplary doses of the pharmaceutical formulations can include about 50-200 mg/kg, for example, about 100 mg/kg daily doses.

Following successful treatment, it may be desirable to have the subject undergo maintenance therapy to prevent the recurrence of the disease or malignant condition treated.

iii. Scheduling

Dosing schedules can be calculated from measurements of polypeptides in the body of a subject. In general, dosage is from 1 ng to 1,000 mg per kg of body weight and may be given once or more daily, semiweekly, weekly, biweekly, semimonthly, monthly, bimonthly or yearly, as needed or appropriate. Persons of ordinary skill in the art can easily determine optimum dosages, dosing methodologies and repetition rates. One of skill in the art will be able to determine optimal dosing for administration of a polypeptide or polypeptide composition of the present invention to a human being following established protocols known in the art and the disclosure herein.

Single or multiple administrations of the pharmaceutical formulations may be administered depending on the dosage and frequency as required and tolerated by the patient. In any event, the composition should provide a sufficient quantity of the polypeptides of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

The daily dose can be administered once per day or divided into subdoses and administered in multiple doses, e.g., twice, three times, or four times per day. However, as will be appreciated by a skilled artisan, compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

Thus, a pharmaceutical formulation thereof for intravenous administration would be about 0.01 to 100 mg/kg per patient per day. Dosages from 0.1 up to about 1000 mg/kg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington: The Science and Practice of Pharmacy*, 21$^{st}$ Ed., 2006, Lippincott Williams & Wilkins.

To achieve the desired therapeutic effect, pharmaceutical formulations may be administered for multiple days at the therapeutically effective daily dose. Thus, therapeutically effective administration of compositions to treat a disease or malignant condition described herein in a subject may require periodic (e.g., daily) administration that continues for a period ranging from three days to two weeks or longer. Typically, compositions will be administered for at least three consecutive days, often for at least five consecutive days, more often for at least ten, and sometimes for 20, 30, 40 or more consecutive days, or longer, as needed. While consecutive daily doses are a preferred route to achieve a therapeutically effective dose, a therapeutically beneficial effect can be achieved even if the compounds or compositions are not administered daily, so long as the administration is repeated frequently enough to maintain a therapeutically effective concentration of the composition in the subject. For example, one can administer a composition every other day, every third day, or, if higher dose ranges are employed and tolerated by the subject, once a week.

c. Combination Therapies with Established Anticancer Therapies i. Chemotherapy

The bladder cancer-specific peptide ligands described herein can be co-administered with other agents as combination therapies.

Examples of chemotherapeutic agents that can be co-administered with the bladder cancer-specific peptide ligands include without limitation alkylating agents (cisplatin, carboplatin, and oxaliplatin); anti-metabolites (purine or pyrimidine mimetics including for example azathioprine and mercaptopurine); plant alkaloids and terpenoids (vinca alkaloids and taxanes); vinca alkaloids (vincristine, vinblastine, vinorelbine, and vindesine); podophyllotoxin (including etoposide and teniposide); taxanes (paclitaxel, taxol and docetaxel); topoisomerase inhibitors (Type I inhibitors: camptothecins, irinotecan and topotecan; Type II Inhibitors: amsacrine, etoposide, etoposide phosphate, and teniposide); antineoplastics (dactinomycin, doxorubicin, epirubicin, fludarabine and bleomycin). Any chemotherapeutic agent being used to treat the cancer of interest can be co-administered in a combination therapy regime with the bladder cancer-specific peptide ligands.

ii. Radiation

The bladder cancer-specific peptide ligands can be administered in conjunction with radiological procedures. A variety of radiological procedures are available for disease treatments. Any of the procedures know by one of skill can be combined with the polypeptides of the present invention for treatment of a patient. Radiological procedures comprise treatment using radiation therapy to damage cellular DNA. The damage to the cellular DNA can be caused by a photon, electron, proton, neutron, or ion beam directly or indirectly ionizing the atoms which make up the DNA chain. Indirect ionization occurs due to the ionization of water, forming free radicals, notably hydroxyl radicals, which then subsequently damage the DNA. In the most common forms of radiation therapy, the majority of the radiation effect is through free radicals. Due to cellular DNA repair mechanisms, using agents that induce double-strand DNA breaks, such as radiation therapies, has proven to be a very effective technique for cancer therapy. Cancer cells are often undifferentiated and stem cell-like, such cells reproduce more rapidly and have a diminished ability to repair sub-lethal damage compared healthy and more differentiated cells. Further, DNA damage is inherited through cell division, leading to an accumulation of damage to the cancer cells, inducing slower reproduction and often death.

The amount of radiation used in radiation therapy procedure is measured in gray (Gy), and varies depending on the type and stage of cancer being treated and the general state of the patient's health. The dosage range can also be affected by cancer type, for example, the typical curative dosage for a solid epithelial tumor ranges from 60 to 80 Gy, while the dosage for lymphoma ranges from 20 to 40 Gy.

Preventative (adjuvant) doses can also be employed and typically range from 45 to 60 Gy administered in 1.8 to 2 Gy fractions (for breast, head and neck cancers). Many other factors are well-known and would be considered by those of skill when selecting a dose, including whether the patient is receiving other therapies (such as for example, but not limited to administration of the bladder cancer-specific peptide ligands, administration of chemotherapies and the like), patient co-morbidities, timing of radiation therapy (for example, whether radiation therapy is being administered before or after surgery), and the degree of success of any surgical procedures.

Delivery parameters of a prescribed radiation dose can be determined during treatment planning by one of skill. Treatment planning can be performed on dedicated computers using specialized treatment planning software. Depending on the radiation delivery method, several angles or sources may be used to sum to the total necessary dose. Generally, a plan is devised that delivers a uniform prescription dose to the tumor and minimizes the dosage to surrounding healthy tissues.

iii. Surgery

The bladder cancer-specific peptide ligands can be administered in conjunction with surgical removal or debulking of tumors. A variety of surgical procedures are available for disease treatments. Any of the procedures know by one of skill can be combined with the polypeptides of the present invention for treatment of a patient. Surgical procedures are the commonly categorized by urgency, type of procedure, body system involved, degree of invasiveness, and special instrumentation.

Examples of surgical procedure can include emergency as well as scheduled procedures. Emergency surgery is surgery that must be done quickly to save life, limb, or functional capacity. Further examples of surgical procedures can include exploratory surgery, therapeutic surgery amputation, replantation, reconstructive, cosmetic, excision, transplantation or removal of an organ or body part, as well as others know in the art. Exploratory surgery can be performed to aid or confirm a diagnosis. Therapeutic surgery treats a previously diagnosed condition. Amputation involves cutting off a body part, usually a limb or digit. Replantation involves reattaching a severed body part. Reconstructive surgery involves reconstruction of an injured, mutilated, or deformed part of the body. Cosmetic surgery can done to improve the appearance of an otherwise normal structure or for repair of a structure damaged or lost due to disease. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

In addition to traditional open surgical procedure that employ large incisions to access the area of interest, surgery procedures further include minimally invasive surgery. Minimally invasive surgery typically involves smaller outer incision(s) which are employed for insertion of miniaturized instruments within a body cavity or structure, as in laparoscopic surgery or angioplasty. Laser surgery involves the use of a laser for cutting tissue instead of a scalpel or similar surgical instruments. icrosurgery involves the use of an operating microscope for the surgeon to see small structures. Robotic surgery makes use of a surgical robot (such as for example the Da Vinci (Intuit Surgical, Sunnyvale, Calif.)), to control the instrumentation under the direction of one of skill, such as for example a surgeon.

5. Methods of Monitoring Efficacy of Treatment

A variety of methods can be employed in determining efficacy of therapeutic and prophylactic treatments with the bladder cancer-specific peptide ligands described herein. Generally, efficacy is the capacity to produce an effect without significant toxicity. Efficacy indicates that the therapy provides therapeutic or prophylactic effects for a given intervention (examples of interventions can include by are not limited to administration of a pharmaceutical formulation, employment of a medical device, or employment of a surgical procedure). Efficacy can be measured by comparing treated to untreated individuals or by comparing the same individual before and after treatment. Efficacy of a treatment can be determined using a variety of methods, including pharmacological studies, diagnostic studies, predictive studies and prognostic studies. Examples of indicators of efficacy include but are not limited to inhibition of tumor cell growth and promotion of tumor cell death.

The efficacy of an anti-cancer treatment can be assessed by a variety of methods known in the art. The bladder cancer-specific peptide ligands can be screened for prophylactic or therapeutic efficacy in animal models in comparison with untreated or placebo controls. The bladder cancer-specific peptide ligands identified by such screens can be then analyzed for the capacity to induce tumor cell death or enhanced immune system activation. For example, multiple dilutions of sera can be tested on tumor cell lines in culture and standard methods for examining cell death or inhibition of cellular growth can be employed. (See, e.g., Maniatis, et al., *Molecular Cloning: A Laboratory Manual*, Cold Spring Harbor Lab., New York, 1982; Ausubel, et al. Editor, *Current Protocols in Molecular Biology*, USA, 1984-2008; and Ausubel, et al. Editor, *Current Protocols in Molecular Biology*, USA, 1984-2008; Bonifacino, et al., Editor, *Current Protocols in Cell Biology*, USA, 2010; all of which are incorporated herein by reference in their entirety.)

The methods of the present invention provide for detecting inhibition disease in patient suffering from or susceptible to various cancers. A variety of methods can be used to monitor both therapeutic treatment for symptomatic patients and prophylactic treatment for asymptomatic patients.

Monitoring methods can entail determining a baseline value of a tumor burden in a patient before administering a dosage of the bladder cancer-specific peptide ligands, and comparing this with a value for the tumor burden after treatment, respectively.

With respect to therapies using the bladder cancer-specific peptide ligands, a significant decrease (i.e., greater than the typical margin of experimental error in repeat measurements of the same sample, expressed as one standard deviation from the mean of such measurements) in value of the tumor burden signals a positive treatment outcome (i.e., that administration of the bladder cancer-specific peptide ligands has blocked or inhibited, or reduced progression of tumor growth and/or metastasis). In some embodiments, treatment with the bladder cancer-specific peptide ligands is considered to be efficacious if the tumor burden in the subject being treated is reduced by at least about 10%, for example, by at least about 20%, 30%, 40% or 50%, or by completely eliminating the tumor burden, e.g., comparing tumor burden before and after treatment in the subject.

In other methods, a control value of tumor burden (e.g., a mean and standard deviation) is determined from a control population of individuals who have undergone treatment with the bladder cancer-specific peptide ligands. Measured values of tumor burden in a patient are compared with the control value. If the measured level in a patient is not significantly different (e.g., more than one standard deviation) from the control value, treatment can be discontinued. If the tumor burden level in a patient is significantly above the control value, continued administration of agent is warranted.

In other methods, a patient who is not presently receiving treatment but has undergone a previous course of treatment is monitored for tumor burden to determine whether a resumption of treatment is required. The measured value of tumor burden in the patient can be compared with a value of tumor burden previously achieved in the patient after a previous course of treatment. A significant decrease in tumor burden relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant increase in tumor burden relative to the control level (i.e., more than a standard deviation) is an indicator that treatment should be resumed in a patient.

The tissue sample for analysis is typically blood, plasma, serum, mucous, tissue biopsy, tumor, ascites or cerebrospinal fluid from the patient. The sample can be analyzed for indication of neoplasia. Neoplasia or tumor burden can be detected using any method known in the art, e.g., visual observation of a biopsy by a qualified pathologist, or other visualization techniques, e.g., radiography, ultrasound, magnetic resonance imaging (MRI).

6. Methods of Diagnosis a. Patients Subject to Diagnosis

The binding of the bladder cancer-specific peptide ligands find use in the detection and diagnosis of bladder cancer in a subject. The present bladder cancer-specific ligands can bind to integrin $\alpha 5\beta 3$ and integrin $\alpha 5\beta 5$, on the surface of a cell.

The binding levels of the bladder cancer-specific peptide ligands can be determined on bladder tissue suspected of being cancerous. To determine whether the bladder cancer-specific peptide ligands bind to bladder tissue, a tissue biopsy of bladder tissue may be taken. In other embodiments, binding of the bladder cancer-specific peptide ligands to bladder cells in a urine sample are determined.

Accordingly, patients who can benefit from the present method may already present with symptoms of bladder cancer. For example, evidence of bladder cancer or a tumor may be present (by visual inspection or palpation, or by scanning techniques, e.g., magnetic resonance imaging (MRI) or Positron Emission Tomography (PET) scans).

The present diagnostic methods find use in conjunction with presently available diagnostic tests for cancer. The patient may already have a preliminary diagnosis of cancer, e.g., based on a serum biomarker, a urinary biomarker or a genetic analysis. Biomarkers that facilitate a diagnosis of bladder cancer are known in the art, and described, e.g., in Netto and Epstein, *Pathology*. (2010) 42(4):384-94; Gaston and Grossman, *Methods Mot Biol*. (2010) 641:303-23; Goebell, et al., *Urologe A*. (2010) 49(4):547-59; Mowatt, et al., *Health Technol Assess*. (2010) 14(4):1-331; Mitra and Cote, *Nat Rev Urol*. (2010) 7(1):11-20; Bryan, et al., *BJU Int*. (2010) 105(5):608-13; Apolo, et al., *Future Oncol*. (2009) 5(7):977-92. In such cases, a biopsy may be justified and detection of the binding levels of the bladder cancer-specific peptide ligands or the expression levels of integrin $\alpha 5\beta 3$ and/or integrin $\alpha 5\beta 5$ in the tissue suspected of being cancerous can confirm or contradict a preliminary diagnosis of cancer.

In other cases, the patient may have a personal or familial history of bladder cancer or a cancer of another urological tissue. For example, the patient may be in remission following successful therapeutic treatment of the bladder cancer. The patient may also have tested positive for a gene associated with increased risk of bladder cancer or the recurrence of bladder cancer.

b. Obtaining a Biological Sample

The biological sample from which the expression levels are measured will depend on the tissue suspected on being cancerous. Usually, the biological sample is from the tissue suspected of being cancerous, e.g., bladder cells or bladder tissue.

In some embodiments, the biological sample is a urine sample. Bladder cells can slough off from bladder tissue and be expelled in urine. Urine cytology can be performed on a sample of voided urine or at the time of cystoscopy ("bladder washing"). Urine cytology relies on pathologic analysis of malignant cells shed into the urine during local tumor growth (Sullivan, et al., *Am J Transl Res*. (2010) 2(4):412-40; Caraway, et al., *Cancer Cytopathol*. (2010) 118(4):175-83). The specimen is usually obtained via voiding or from bladder washing during an endoscopic procedure. Urine cytology can be used in combination with urethrocystoscopy to detect bladder cancers in persons deemed to be at high risk, particularly when urinalysis reveals clinically relevant hematuria. Bladder cells in a urine sample can be concentrated, e.g., by centrifugation, and then contacted with a bladder cancer-specific peptide.

In some embodiments, the biological sample is from a biopsy. In some embodiments, the biological sample is epithelial bladder tissue. In certain instances, for example, the determination of the presence of bladder cancer metastasis, it may be appropriate for the biological sample to be from a tissue other than bladder tissue.

In some embodiments, it may be appropriate to measure bladder cancer-specific peptide ligand binding levels in a tissue different from the tissue suspected of being cancerous, e.g., to determine the presence of metastasis.

c. Determining the Presence of Bladder Cancer

The level of binding of the bladder cancer-specific peptide ligands can be measured according to methods well known in the art, and described herein. The level of peptide ligand binding can be detected, for example, using directly or indirectly labeled detection agents, e.g., fluorescently, radioactively or enzymatically labeled bladder cancer-specific peptide ligands. For example, the peptides can be conjugated to labeled beads, e.g., beads that can be detected via a fluorescent label, a chemiluminescent label, a quantum dot label, or any other label known in the art. Assays using labeled beads are well known in the art.

To provide an illustrative example, a urine sample is obtained from the subject, and cells in the sample concentrated, e.g., by centrifugation. The concentrated cells from the urine sample, including bladder cells, are then contacted with a bladder cancer-specific peptide ligand, as described herein. Alternatively, the bladder cancer specific peptide ligand is added to the urine sample without first concentrating the cells. The cells can be concentrated after exposure to the peptide. The peptides can be directly labeled, e.g., by conjugation or attachment to a labeled bead. For example, the bead can be labeled with a fluorophore, a chemiluminescent moiety or a quantum dot, or any other detectable label. Peptides conjugated to a bead facilitate detection of binding of the peptide ligands to cancer cells in the urine sample and concentration of bladder cancer cells bound to the peptide ligands. The presence of labeled cells can then be detected and quantified. For example, cells coated with beads conjugated to a bladder cancer-specific peptide ligand can be detected using a microscope or by flow cytometry.

In some embodiments, the bladder cancer-specific ligands are linked (e.g., via chemical linkage or fusion) to a known epitope for antibody binding (e.g., FLAG-tag or c-myc epitopes). Peptide ligands alone or linked to an antibody epitope can be measured using immunoassays known in the art, including immunohistochemical staining, Western blotting, ELISA and the like with an antibody that selectively binds to antibody epitope or a fragment thereof. Detection of peptides using antibodies in immunoassays is known in the art (see, e.g., Harlow & Lane, *Using Antibodies: A Laboratory Manual* (1998); Coligan, et al., eds., *Current Protocols in Immunology* (1991-2010); Goding, *Monoclonal Antibodies: Principles and Practice* (3rd ed. 1996); and Kohler & Milstein, *Nature* 256:495-497 (1975).

Binding levels of the bladder cancer-specific peptide ligands to bladder cells or bladder tissue suspected of being cancerous can be detected using any method known in the art. Exemplary methods include flow cytometry, tissue lysate detection, Western immunoblot and immunohistochemistry.

To provide an illustrative example, a bladder tissue sample (e.g., a biopsy) is incubated with an antibody that specifically binds to the bladder cancer-specific peptide ligand, alone or linked to an epitope tag, under conditions (i.e., time, temperature, concentration of sample) sufficient to allow specific binding. The tissues optionally can be fixed (e.g., in formaldehyde) and permeabilized prior to incubation with antibody. The anti-peptide antibodies can be exposed to a tissue sample for about 0.5, 1.0, 1.5, 2.0, 2.5, 3.0 hours, or overnight, about 8, 10 or 12 hours, as appropriate. However, incubation time can be more or less depending on, e.g., the composition of the antigen, the dilution of the sample and the temperature for incubation. Incubations using less diluted samples and higher temperatures can be carried out for shorter periods of time. Incubations are usually carried out at room temperature (about 25° C.) or at biological temperature (about 37° C.), and can be carried out in a refrigerator (about 4° C.). Washing to remove unbound sample before addition of a secondary antibody is carried according to known immunoassay methods.

The bladder cancer-specific peptide ligands can be directly labeled or labeled secondary antibodies can be used to detect antibodies in a sample that have bound to the peptide ligands. Secondary antibodies bind to the constant or "C" regions of different classes or isotypes of immunoglobulins—IgM, IgD, IgG, IgA, and IgE. Usually, a secondary antibody against an IgG constant region is used in the present methods. Secondary antibodies against the IgG subclasses, for example, IgG1, IgG2, IgG3, and IgG4, also find use in the present methods. Secondary antibodies can be labeled with any directly or indirectly detectable moiety, including a fluorophore (i.e., fluoroscein, phycoerythrin, quantum dot, Luminex bead, fluorescent bead), an enzyme (i.e., peroxidase, alkaline phosphatase), a radioisotope (e.g., $^{3}$H, $^{32}$P, $^{125}$I, $^{123}$I, $^{11}$C, $^{13}$N, $^{15}$O, $^{18}$F, $^{82}$Rb, technetium-99m (Tc-99m), thallium-201) or a chemiluminescent moiety. Labeling signals can be amplified using a complex of biotin and a biotin binding moiety (i.e., avidin, streptavidin, neutravidin). Fluorescently labeled anti-human IgG antibodies are commercially available from Molecular Probes, Eugene, Oreg. Enzyme-labeled anti-human IgG antibodies are commercially available from Sigma-Aldrich, St. Louis, Mo. and Chemicon, Temecula, Calif.

The method of detection of the levels of binding of the bladder cancer-specific peptide ligands in a sample will correspond with the choice of label of the secondary antibody. For example, if tissue lysates containing bound to the peptide ligands are transferred onto a membrane substrate suitable for immunoblotting, the detectable signals (i.e., blots) can be quantified using a digital imager if enzymatic labeling is used or an x-ray film developer if radioisotope labeling is used. Likewise, tissue samples subject to immunohistochemistry can be evaluated using immunofluorescence microscopy or a scanning microscope and automated scanning software capable of detecting and quantifying fluorescent, chemiluminescent, and/or colorimetric signals. Such methods of detection are well known in the art and are described herein.

General immunoassay and immunohistochemical techniques are well known in the art. Guidance for optimization of parameters can be found in, for example, Wu, *Quantitative Immunoassay: A Practical Guide for Assay Establishment, Troubleshooting, and Clinical Application*, 2000, AACC Press; *Principles and Practice of Immunoassay*, Price and Newman, eds., 1997, Groves Dictionaries, Inc.; *The Immunoassay Handbook*, Wild, ed., 2005, Elsevier Science Ltd.; Ghindilis, Pavlov and Atanassov, *Immunoassay Methods and Protocols*, 2003, Humana Press; Harlow and Lane, *Using Antibodies: A Laboratory Manual*, 1998, Cold Spring Harbor Laboratory Press; *Immunoassay Automation: An Updated Guide to Systems*, Chan, ed., 1996, Academic Press; Dabbs, *Diagnostic Immunohistochemistry: Theranostic and Genomic Applications*, 2010, Saunders; Renshaw, *Immunohistochemistry: Methods Express Series*, 2007, Scion Publishing Ltd.; and Buchwalow and Böcker, *Immunohistochemistry: Basics and Methods*, 2010, Springer.

The presence of binding or of increased binding of the bladder cancer-specific peptide ligands is indicated by a detectable signal (i.e., a blot, fluorescence, chemiluminescence, color, radioactivity) in an immunoassay or immunohistochemical assay, where the biological sample from the patient is contacted with antibody or antibody fragment that specifically binds to the peptide ligand or epitope tag.

Detectable signal can be compared to the signal from a normal or non-cancerous control sample from bladder tissue or bladder cells or to a threshold value. In some embodiments, the presence of binding or of increased binding of the bladder cancer-specific peptide ligands is detected, and the presence or increased risk of cancer is indicated, e.g., when the detectable signal of peptide ligand binding levels in the test sample is at least about 10%, 20%, 30%, 50%, 75% greater in comparison to the signal of peptide ligand binding levels in the normal or non-cancerous control sample or the predetermined threshold value. In some embodiments, an increased binding level of the bladder cancer-specific ligand is detected, and the presence or an increased risk of cancer is indicated, when the detectable signal of bladder cancer-specific peptide ligand binding level in the test sample is at least about 1-fold, 2-fold, 3-fold, 4-fold or more, greater in comparison to the signal of bladder cancer-specific peptide ligand binding level in the normal or non-cancerous control sample or the predetermined threshold value. Usually, the sample and control or predetermined threshold levels are from the same tissue types.

In some embodiments, the bladder cancer-specific peptide ligand binding level is compared with bladder cancer-specific peptide ligand binding levels in a control tissue or control cells known to be cancerous. In this case, the bladder cancer-specific peptide ligand binding level in the test biological sample equivalent to or greater than the positive control sample, known to be cancerous, is indicative of cancer. Usually, the sample and control or predetermined threshold levels are from the same tissue types (e.g., bladder tissue).

Alternatively, if the bladder cancer-specific peptide ligand binding levels in the test biological sample are less than the bladder cancer-specific peptide ligand binding levels in the positive cancerous tissue control or the predetermined threshold level, then a diagnosis of cancer is generally not indicated. Likewise, if the bladder cancer-specific peptide ligand binding levels in the test biological sample are equivalent to or less than a normal or non-cancerous control or the predetermined threshold level, then a diagnosis of cancer is not indicated.

In some embodiments, the results of the bladder cancer-specific peptide ligand binding level determinations are recorded in a tangible medium. For example, the results of the present diagnostic assays (e.g., the observation of the presence or increased presence of bladder cancer-specific peptide ligand binding) and the diagnosis of whether or not the presence or an increased risk of cancer is determined can be recorded, e.g., on paper or on electronic media (e.g., audio tape, a computer disk, a CD, a flash drive, etc.).

In some embodiments, the methods further comprise the step of providing the diagnosis to the patient of whether or not there is the presence or an increased risk of cancer in the patient based on the results of the bladder cancer-specific peptide ligand binding level determinations.

In some embodiments, the methods further comprise the step of providing or recommending an appropriate course of treatment to the patient based on the results of the bladder cancer-specific peptide ligand binding level determinations.

Methods of determining the presence of bladder cancer in a subject based on the binding of the bladder cancer-specific peptide ligands described herein to a biological sample containing bladder cells or bladder tissue can be performed in conjunction with other known methods of diagnosing bladder cancer.

7. Methods of in situ Imaging

The bladder cancer-specific peptide ligands described herein find use in methods of local visualization of bladder cancer, for example, during transurethral resection of bladder cancer (TURBT). A bladder cancer-specific peptide ligand conjugated to a fluorescent dye finds use for this application.

Another application of the bladder cancer-specific peptide ligands described herein is imaging detection of bladder cancer that can supplement or decrease intrusive and costly cystoscopy. Magnetic resonance imaging (MRI) and positron emission tomography (PET) can be performed in a subject suspected of having or known to have bladder cancer. Both MRI and PET scans have been widely used for the diagnosis of malignancies, and find use in the diagnosis and detection of bladder malignancies. Therefore, MRI and PET or single photon emission computed tomography (SPECT) can be used to facilitate the detection of bladder cancer using the bladder cancer-specific peptide ligands described herein conjugated to imaging agents, for example, an iron oxide for MRI and a radioisotope for PET/SPECT (e.g., $^{123}$I, $^{11}$C, $^{13}$N, $^{15}$O, $^{18}$F, $^{82}$Rb, technetium-99m (Tc-99m), thallium-201).

In order to allow for in situ imaging, the bladder cancer specific peptide ligands attached to an appropriate imaging agent are contacted with the tissue suspected of containing or known to contain bladder cancer cells within the subject. By performing an appropriate imaging methodology on the patient, the location and extent of bladder cancer cells in the imaged tissue can be determined.

In some embodiments, the methods further comprise removing, resecting or excising the bladder cancer cells from the tissue, e.g., based on detecting the binding of the bladder cancer-specific peptide ligands. Magnetic particles conjugated to a bladder cancer-specific peptide ligand can further be used for the extraction and removal of bladder cancer cells. Use of magnetic nanoparticle-peptide conjugates for the in vitro and in vivo targeting and extraction of cancer cells is described, e.g., in Scarberry, et al., *J Am Chem Soc* (2008) 130(31):10258-10262.

8. Kits

The present invention also provides for kits comprising a bladder cancer-specific peptide ligand, as described herein. The embodiments of the bladder cancer-specific peptide ligand in the kits are as described herein. In some embodiments, the bladder cancer-specific peptide ligand is conjugated to or attached to a labeled bead.

In addition the kits will typically include instructional materials disclosing means of use of the bladder cancer-specific peptide ligand. In the kits, the bladder cancer-specific ligands may be formulated for administration, and provided in one or multiple unit doses. The kits may also include additional components to facilitate the particular application for which the kit is designed. The kits may additionally include buffers and other reagents routinely used for the practice of a particular method. Such kits and appropriate contents are well known to those of skill in the art.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are offered to illustrate, but not to limit the claimed invention.

Example 1: Discovery of Bladder Cancer Specific Ligands

Materials and Methods
Synthesis of the Initial and Focused OBOC Libraries.
OBOC libraries were synthesized on solid phase TentaGel S NH2 resin (Rapp Polymere Gmbh, Germany) by a "split-mix synthesis" method (Lam, et al., *Nature*, (1991) 354: 82-84; Lam, et al., *Chem Rev*, (1997) 97: 411-448; and .Peng, et al., *Nat Chem Biol*, (2006) 2: 381-389). The peptide moiety of the peptidomimetic was synthesized by standard solid-phase peptide synthesis techniques using 9-fluorenylmethoxycarbonyl (Fmoc) chemistry and N-hydroxybenzotriazole (HOBt)/N,N'-diisopropylcarbodiimide (DIC) coupling. And, the completion of coupling was confirmed with a ninhydrin test. The beads were stored in 70% ethanol at 4° C. until use.

Cells

Four bladder cancer cell lines including 5637 (HTB-9), SCaBER, TCCSUP (HTB-5), and T24 (HTB-4) were purchased from the American Type Culture Collection (Manassas, Va.). The isolation, characterization and maintenance of normal urothelial cells was previously described in detail (Bagai, et al., *J Biol Chem*, (2002) 277: 23828-23837). Normal peripheral blood mononuclear cells were prepared by using the Ficoll-Paque gradient method from peripheral blood of healthy donors. Bladder cancer tissue obtained from cystectomy was cut into pieces, digested with collagenase at 37° C. for 1-2 hours per the manufacturer's protocol, and filtered through a 40-µm strainer to make single cell suspension. Tumor cells were then isolated with Ficoll-Paque gradient method (800 g, 30 min at 4° C.). Informed consent was obtained from each patient or healthy donor before specimens were collected.

Five canine bladder transitional cell lines labeled K9TCC, K9TCC-AxA, K9TCC-AxC, K9TCC-Nk and K9TCC-In were kindly provided by Deborah W. Knapp at Purdue University (Dhawan, et al., *Urol Oncol*, (2009) 27: 284-292). These cells were maintained in DMEM/F12, with 10% FBS and 2 mM glutamine, and incubated in 5% $CO_2$ at 37° C.

Screening of OBOC Library for Bladder Cancer-specific Ligands

The beads were washed extensively with double-distilled water and phosphate-buffered saline (PBS) before screening. Bladder cancer cells and normal urothelial cells were detached from culture dishes with trypsin/EDTA or a Detach kit (PromoCell, Heidelberg, Germany), washed with their corresponding culture medium, resuspended at $10^6$ cells/ml and incubated with OBOC beads in Petri dishes in a humidified $CO_2$ incubator at 37° C. with shaking (60 rpm). Beads bound by cells appeared as rosettes with a central bead covered by a layer(s) of cells under a microscope. The positive beads were picked with a pipette under inverted microscope, treated with Quanidine HCl (8M, 20 min) to remove cells and proteins on beads surface, and underwent a second round of incubation with the same cells to confirm the binding. Only those beads with cell bindings at both rounds were sent for the amino acid sequencing as previously described (Peng, et al., *Nat Chem Biol*, (2006) 2: 381-389).

Synthesis of Peptide and Peptide-Biotin.

The synthetic chemistry of solution phase PLZ4 and PLZ4-biotin for biological testing is similar to that of the library using HOBt/DIC coupling. Rink amide resin was used as solid support to prepare compounds with carboxyl amide.

Fluorescence Microscopy.

Bladder cancer cells and normal urothelial cells ($2\times10^4$ cells each well) were seeded on chamber slides. When the cells grew confluent over 70%, they were washed with PBS and blocked with 3% BSA-PBS at 4° C. for 1 hour, and incubated with the peptide-biotin conjugate (1 µM) for 1 h at 4° C. in TBS buffer. Cells were then washed three times with TBS and incubated with FITC-Streptavidin (0.5 µg/ml) (ZYMED, South San Francisco, Calif.). Cells were washed and examined using an inverted Olympus fluorescence microscope (20×).

Flow Cytometry.

All of the following steps were done on ice. $5\times10^5$ 5637 cells were washed 3 times with 1 ml cold PBS (pH 7.4)-BSA (1%), re-suspended with 300 µl cold BSA (5%)-PBS (pH 7.4), and then incubated for 1 hour on ice. The cells were centrifuged and suspended with 50 µl PLZ4-biotin solution at 800, 400, 200, 100, 50, 25, 10, 5, 2.5, 1, 0.1, and 0 µM, and incubated for 1 hour on ice. Cells treated without PLZ4-biotin was considered as a control. After washing 6 times with 1 ml cold PBS-Tween-20 (0.05%) buffer, cells were re-suspended with 50 µl streptavidin (SA)-PE (1:500 in PBS-BSA, 1%) (1 mg/ml, Invitrogen, Carlsbad, Calif.), incubated for 1 hour on ice, washed with PBS (pH 7.4) 3 times, re-suspended with 500 µl PBS (pH 7.4), and analyzed using a Coulter Epics XL-MCL flow cytometer (Beckman Coulter, Inc.). The experiment was repeated three times. The mean value was expressed in FIG. 4.

In Vivo and Ex Vivo Mouse Imaging.

The PLZ4-CY5.5 conjugate was prepared by incubating PLZ4-biotin conjugates with streptavidin (SA)-CY5.5 (Rockland Immunochemicals, Gilbertsville, Pa.). One streptavidin can bind up to 4 molecules of biotin. To ensure at least one PLZ4-biotin molecule binds to SA-CY5.5, PLZ4-biotin was mixed with SA-Cy5.5 at molar ratios of 5:1 for 1 h at 4° C. The fluorescence labeling was confirmed by in vitro cell-binding assays. Athymic nude mice were purchased from Harlan Laboratories (Indianapolis, Ind.). All experiments were performed in compliance with institutional guidelines and according to protocols. Primary bladder cancer specimens were harvested from cystectomy by a pathologist after informed consent was obtained from patients. This protocol was approved by the UC Davis IRB. Primary cancer tissue was minced and incubated with collagenase at 37° C. for one hour with rotation. Single cell suspension was obtained by straining through a 40 µm strainer. Some of the primary cells were incubated with OBOC beads to determine cell binding (FIG. 3). Primary bladder cancer cells were mixed with matrigel per manufacturer's instruction (BD Biosciences, Sparks, Md.), and subcutaneously injected into one side of the shoulder of mice. Tumors measured about 0.5-1.0 cm in diameter at the time of imaging. Mice were anesthesized using intraperitoneal injection of pentobarbital (60 mg/kg), and performed imaging using a Kodak multimodal-imaging system IS2000MM (Kodak) equipped with an excitation bandpass filter at 625 nm and an emission at 700 nm. Exposure time was 30 s per image. Images were analyzed using the imaging station IS2000MM software (Kodak, Rochester, N.Y.). After in vivo imaging, the mice were euthanized with $CO_2$ overdose. Tumors and other normal organs and tissues were excised and imaged with the Kodak imaging system as described above.

Data Processing and Statistics.

The experiments were repeated in duplicate or triplicate. The mean values were presented here. For determination of tumor contrast, mean fluorescence intensities of the tumor area and of the normal tissue area were calculated by means of the region-of-interest function using Kodak 1D Image Analysis Software (Kodak), then plotted a pseudocolored scale based the semiquantitative information from NIRF images by integrating fluorescence intensities from equal areas within tumor and normal tissue regions (FIG. 5).
Results:
Identification of a Bladder Cancer-specific Ligand Whole cell bead binding assay was used to screen libraries for peptides that bind bladder cancer cell cultures (FIG. 1). Approximately 150,000 library beads (peptides) were screened against each of 4 bladder cancer cell lines (three transitional cell carcinoma (TCC) lines: T24, TCCSUP and 5637, and one squamous cell line SCaBER). The two cyclic random peptide libraries used for screening were 7-mer $cX_1X_2X_3X_4X_5X_6X_7c$ (SEQ ID NO:15) and 5-mer $c(U/Z)_5c$ (SEQ ID NO:16) in which "c" represents D-cysteine, "X" for 19 natural L-amino acids except cysteine, "U" for 8 unnatural amino acids, and "Z" for 17 L-amino acids except arginine, cysteine and lysine. Each peptide contained two flanking D-cysteine residues at the amino and carboxyl ends. These peptides were cyclized by a disulfide bond to more efficiently expose the amino acids in the middle for cell binding. Initially, approximately 150,000 library beads (peptides) were screened with each cell line. Beads with ligands that bound the cancer cell surface receptors became coated with cancer cells. Positive beads (i.e. beads coated with cells) were isolated and underwent a second round of screening with the same cells to eliminate false positive beads.

From this screening, 28 peptides were identified that could bind one of four cell lines. Of these 28 peptides, 21 peptides that bound bladder cancer cells but did not bind to most of 12 cell lines of different origins were selected, and those 21 peptides were screened against primary normal urothelial cells in culture (Bagai, et al., *J Biol Chem*, (2002) 277:23828-23837). One of these ligands with the sequence of cQDGRMGFc (SEQ ID NO:12) bound to all three bladder TCC cell lines (FIG. 2 A-C), but did not bind to normal urothelial cells (FIG. 2D). This ligand was named PLZ4. PLZ4 did not bind to whole blood cells (FIG. 2E), peripheral blood mononuclear cells (PBMC, FIG. 2F) or fibroblasts (FIG. 2G), suggesting these confounding cells inside bladder will not affect the binding of PLZ4 to bladder cancer cells. This is consistent with the observation that PLZ4 did not bind to 10 out of 12 cell lines with different origins. PLZ4 did not bind to cells were isolated from urine specimens collected from 4 consecutive patients who had no evidence of bladder cancer but were actively treated with BCG intravesical therapy (FIG. 2H). This suggests that PLZ4 may not bind to inflamed cells commonly seen in patients treated with BCG.

Beads Coated with PLZ4 can Bind to Bladder Tumor Cells from Patients

The cell surface molecules on established cell lines in culture may not be the same as those molecules on primary bladder cancer cells. It was assessed if PLZ4 could bind to bladder cancer cells from patients. Beads coated with PLZ4 could bind to primary bladder cancer cells from patients (FIGS. 3A and B). So far, PLZ4 could bind to cells from all 5 fresh bladder cancer specimens that were tested. In one patient, both normal tissue and bladder cancer tissue from the same cystectomy specimen were available. Beads coated with PLZ4 could bind to cells from the cancer specimen (FIG. 3B), but not to the cells from the normal specimen of the same bladder (FIG. 3C).

The acidic environment in urine may change the 3-D structure of ligands and affect ligand binding. Here it was determined if the cancer-specific beads could bind to 5637 TCC cancer cells in urine. Cells were incubated with beads in urine at pH 6.0 for 4 hours at 37° C. 4-hour incubation was used to mimic the in vivo urine retention in patients and to permit conformational changes and protease digestion. PLZ4 was still able to bind cells in urine (FIG. 3D).

Dogs naturally develop bladder cancer that is usually invasive. If PLZ4 can bind to canine bladder cancer cells, the preclinical studies can be performed in dogs with naturally occurring bladder cancer before clinical studies in human. Five canine cancer cell lines have been tested. PLZ4-FITC complex could bind to all 5 canine bladder cancer cell lines (FIG. 3E). There was no detectable binding when non-small cell lung cancer cell line A549cells were used or when a leukemia-specific ligand instead of PLZ4 was used in the FITC complex.

Cell Sorting and Fluorescence Detection of Human Bladder Cancer Cells with PLZ4

Figure 4A:
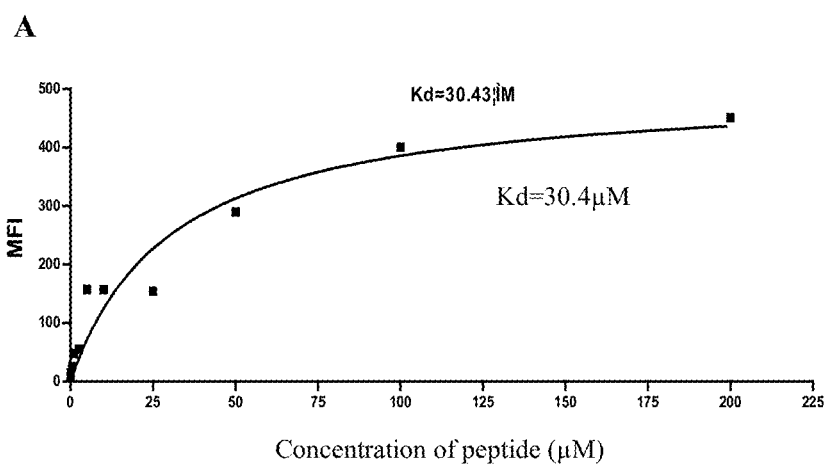
FIG. 4A-B. Fluorescence staining of bladder cancer cells. A. Flow cytometry to determine the binding affinity of PLZ4 to 5637 cells. The fluorescence intensity increased as the concentration of PLZ4-PE increased. This figure represented the mean values of triplicate experiments at each concentration. The binding affinity ($Kd_{50}$) is around 30 µM. B. Fluorescence staining of bladder cancer and normal urothelial cells with PLZ4 conjugated to FITC. Cells were cultured in chamber slides, and stained with PLZ4-FITC. Bladder cancer cells 5637, TCCSUP, and T24 were stained with green, while normal urothelial cells were not stained (the first column from the left). All cell nucleuses were stained blue by DAPI (the second and 4th columns from the left). No cells were stained green when only streptavidin-FITC, but no PLZ4-biotin was added (the third column from the left). Magnification 200×.

Next, it was determined if fluorescence cell sorting could be used to identify bladder cancer cells. PLZ4 peptide conjugated to biotin through hydrophilic linkers was synthesized. Biotinylated PLZ4 was then incubated with streptavidin-PE to generate PLZ4-PE conjugate through the strong binding of biotin and streptavidin. A suspension of freshly trypsinized bladder cancer 5637 cells was incubated with PLZ4-PE conjugate, and underwent flow cytometry cell sorting. concentration-dependent increase of fluorescence on 5637 cells was observed (FIG. 4A). The binding affinity (Kd) is around 30 μM.

Figure 4B:
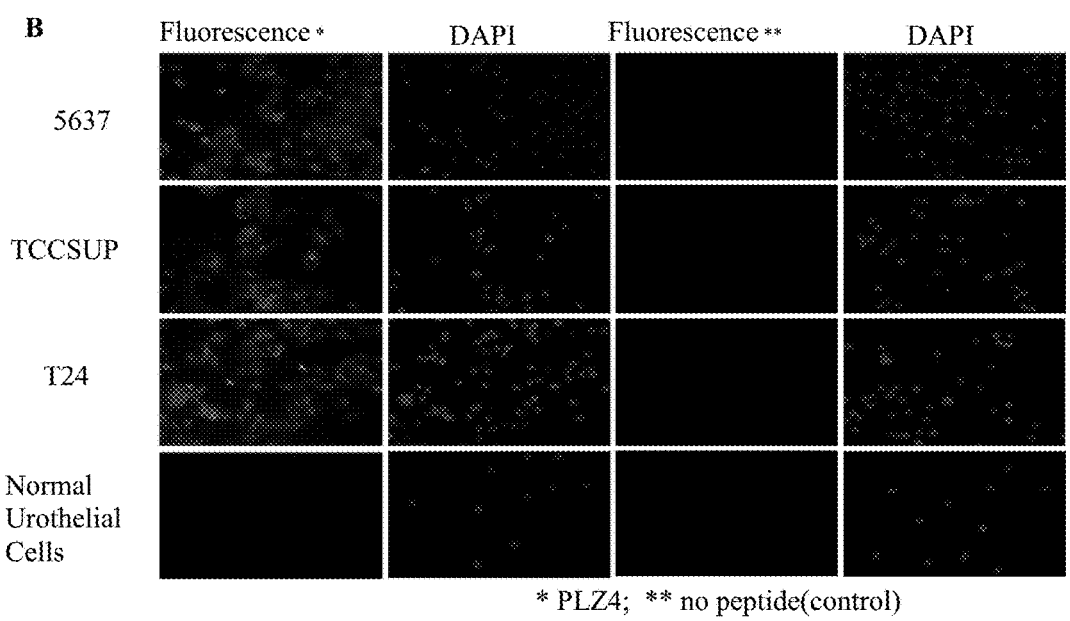

It was then determined if fluorescent-labeled PLZ4 could bind to bladder cancer cells. PLZ4-FITC conjugate were generated using the same approach as that used for the PLZ4-PE conjugate, and used for staining 5637, TCCSUP, T24 and normal urothelial cells growing on chamber slides. In the control experiment, streptavidin-FITC was added without biotinylated ligand. Compared with control cells, strong fluorescence signals could be detected with 5637, TCCSUP and T24 cells under fluorescence microscopy (FIG. 4B). No significant binding was observed on the normal urothelial cells with the same staining condition.

In Vivo Imaging of Nude Mice Bearing Bladder Cancer Xenografts

To investigate if PLZ4 could be used for in vivo bladder cancer detection and targeted therapy, in vivo optical imaging of mice with bladder cancer xenografts developed from primary bladder cancer tissues from patients who underwent cystectomy was used. Near-infrared fluorescent (NIRF) dye Cy5.5 allows an imaging of deeper tissues because the near-infrared light has high penetration, low tissue absorption and scattering rates. When tumor xenografts measured 5-10 mm (4-5 weeks after implantation), PLZ4-Cy5.5 conjugate (7 nmol) was injected via the tail vein. Mice were imaged at 0, 1, 2, 4, 8, 16, 24 hours post inoculation. PLZ4-Cy5.5 uptake by tumors was much higher than that of normal tissue and the tumor area of mice receiving SA-Cy5.5 (FIGS. 5A and B), starting at 2 hr and reaching the greatest difference 4 hr after injection.

To further confirm the in vivo uptake of PLZ4-Cy5.5 complex, ex vivo imaging was performed with excised tumors and organs 24 hours after intravenous injection. The PLZ4-CY5.5 complex accumulated primarily in the tumor xenografts and kidney, whereas no significant uptake was observed in other organs including bladder (FIGS. 5C and D). In the control mouse in which only SA-CY5.5 was injected, strong fluorescent signal (white pseudo-color) was detected in kidneys, suggesting the accumulation of PLZ4-Cy5.5 complex in kidneys may be secondary to the nonspecific uptake or trapping of SA-Cy5.5 by kidney (FIG. 5D). Histochemical staining was performed and confirmed that the tumor xenografts were bladder transitional cells.

Binding of PLZ4 to the Target Integrin

Figure 6A:
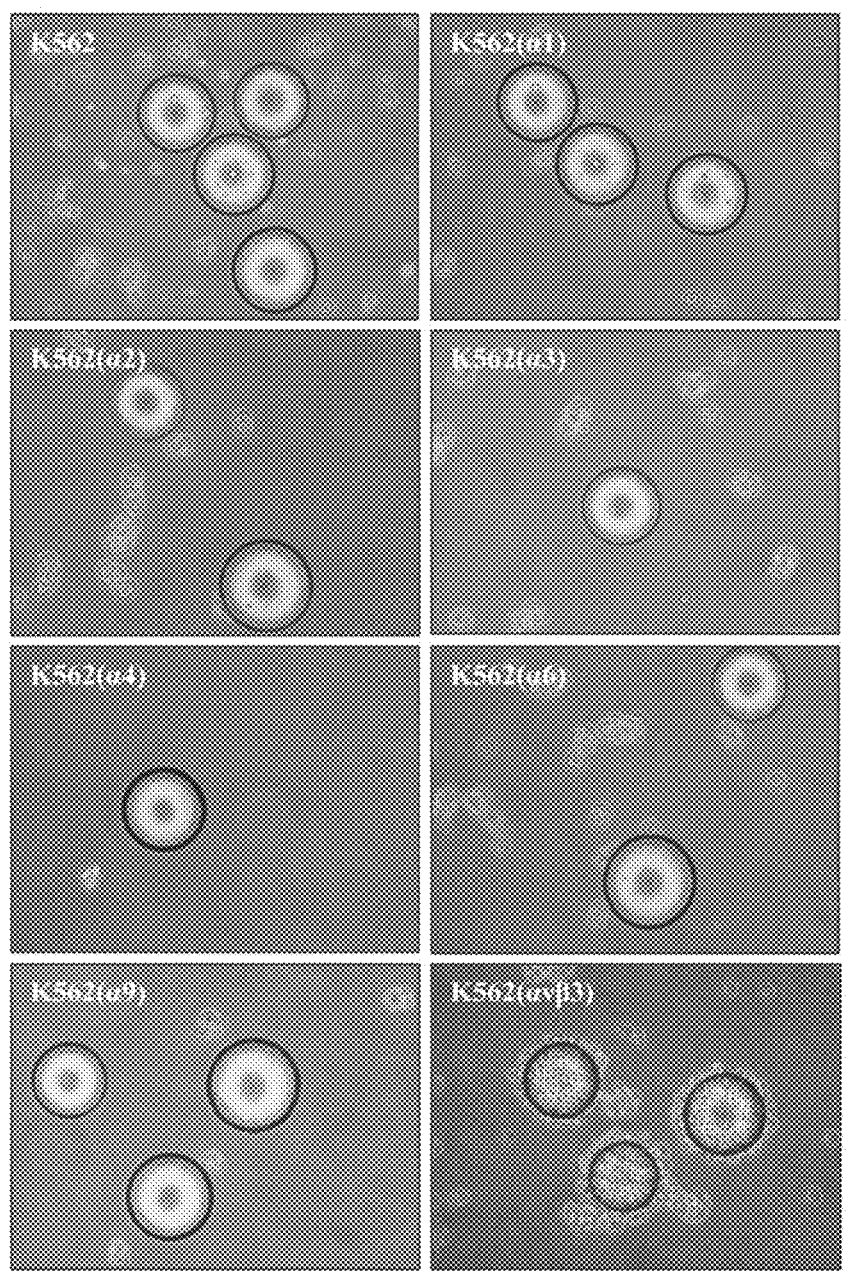
FIG. 6A-C. Binding of PLZ4 to αvβ3 integrin A. PLZ4 binds to αvβ3 integrin. Beads coated with PLZ4 peptides were incubated with K562 cells transfected with different integrin subunits. PLZ4 can only bind to K562 cells when αvβ3 integrin is expressed on the surface. B. Alanine walk to determine the amino acids important for cell binding. Each amino acid in PLZ4 (SEQ ID NO: 5) was replaced with alanine one at a time to generate beads covered with new peptides (SEQ ID NOS 24-30, respectively, in order of appearance) (alanine walk), and tested for their binding to 5637 bladder cancer cells. Semi-quantitative system was used to determine binding activity: ++++ means very strong binding with 75-100% bead surface covered by cells; +++ means strong binding with 50-74% bead surface covered by cells; +++ means moderate binding with 25-49% bead surface covered by cells; + means weak binding with 1-24% bead surface covered by cells; − means no binding. C. The effects of glycine residues at the $X_5$ position on the binding of PLZ4 to bladder cancer cells. The peptides on beads in each panel have the same backbone sequence (cQDGRK-GFc; SEQ ID NO:11) as PLZ4 (cQDGRMGFc; SEQ ID NO:12) except the M at the $X_5$ position has been replaced with K. One (c) to six (h) numbers of glycine were conjugated to K from Panel c to h (SEQ ID NO:13). The OBOC beads were incubated with 5637 TCC cells. Compared with the parental PLZ4 ligand (a), no significant changes in binding to 5637 cells were observed when methionine was replaced with lysine (b). This ligand could still strongly bind to 5637 cells when only one (c) or two (d) glycine residues were added. But there is significant decrease in cell binding when three (e) or four (f) glycines were added, and no binding when five (g) and six (h) glycines were added.
Figure 6B:
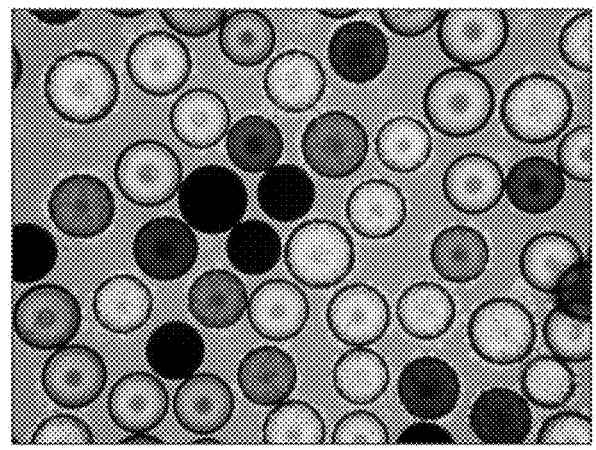
Figure 6C:
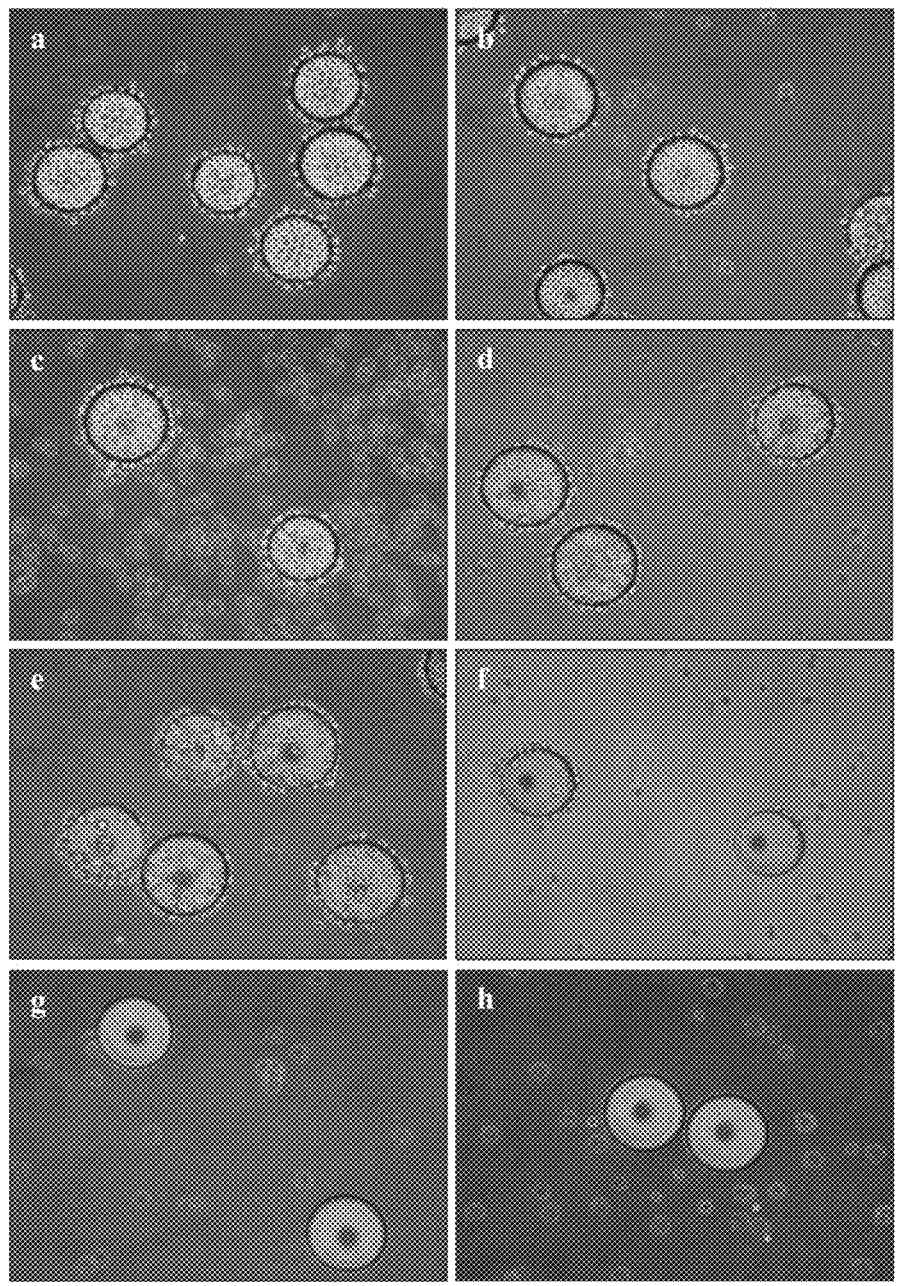

Some studies showed peptides containing the NGR motif bind to integrin. Here, OBOC beads bearing PLZ4 peptides on the surface were incubated with K562 cells transfected with various integrins. K562 cells express endogenous a5β1 integrin. PLZ4 bound to K562 cells transfected with a5β3 integrin, but not to the parental K562 cells or cells transfected other integrins (FIG. 6A). Several other ligands obtained from the initial screening also contain the DGR motif. However, only PLZ4 is bladder cancer-specific, suggesting that other amino acids besides DGR determine the binding specificity. To identify which amino acids are involved in determining cell binding and binding specificity, "alanine walk" was performed combined with the rainbow bead coding methods (Luo, et al., *J Comb Chem*, (2008) 10: 599-604). The amino acids aspartic acid (D, the $X_2$ position), arginine (R, $X_4$) and phenylalanine (F, $X_7$) are important for cell binding. Replacement of any of these amino acids with alanine completely abolished the binding of the peptides to 5637 cells (FIG. 6B). The glycine residues (G) at the $X_3$ and $X_6$ positions are important for cell binding because replacement of one of these two amino acids significantly decreased but did not abolish the binding of the peptides to 5637 cells. Methionine at the $X_5$ position could be replaced to many other amino acids without compromising the binding affinity. Based on this analysis, the three amino acids (D, G and R) at the N-terminus together with the two amino acids (G and F) at the C-terminus determine the binding specificity. Therefore, the binding pocket may be in the clover shape: one for the N-terminal three amino acids, one for the C-terminal two amino acids and a middle pocket. So w the depth of the middle binding pocket by adding different numbers of glycine residue to the $X_5$ position. Two glycine residues could be added to fill in the central pocket without significant effect on cell binding (FIG. 6C). Addition of more than 4 glycines completely abolished the binding of PLZ4 to the target cells.

Discussion

Bladder cancer-specific ligands can improve the diagnosis and management of bladder cancer. First, these ligands can be used for tumor localization. About 75-80% of bladder cancer cases are diagnosed at the non-invasive stages and usually treated with TURBT. However, incomplete resection can be found in about one third of cases regardless of the expertise of the urologists (Herr, *J Urol*, (2005) 174: 2134-2137. 5-aminolevulinic acid (ALA) combined with fluorescence cystoscopy has been used for tumor localization (Daniltchenko, et al., *J Urol*, (2005) 174: 2129-2133). Nonspecific uptake of ALA by non-cancer urothelial cells, especially in inflamed bladder with BCG treatment, causes high background fluorescence that interferes with the detection of cancer by cystoscopy (Grossman, Society of Urological Oncology Winter Meeting 2005 (Podium presentation), Bethesda, Md., 2005). PLZ4 can specifically bind to bladder cancer cells, but not to normal urothelial cells, normal cells from the same bladder that contains cancer, or cells from patients who were actively treated with BCG. It is shown that FITC-conjugated PLZ4 stains bladder cancer cells, suggesting that this ligand can be used for fluorescence detection and tumor localization of non-invasive bladder cancer. Our PLZ4 ligand could bind to cancer cells in urine with pH 6, suggesting that PLZ4 can be used in the acidic urine environment. Because the urinary bladder is relatively isolated from the rest of the human body, intravesical instillation of fluorophor-conjugated cancer-specific ligands will elicit minimal or no undesirable side effects.

Bladder cancer-specific ligands can be used for targeted therapy against non-invasive and advanced bladder cancer. Intravesical instillation of BCG or chemotherapy has been used to reduce the risk of bladder cancer recurrence. However, this therapy is still associated with significant risk of recurrence (Herr, et al., *J Clin Oncol*, (1995) 13: 1404-1408; and Herr, et al., *J Urol*, (1989) 141: 22-29). PLZ4 can be linked to chemotherapy drugs for targeted therapy, either through intravesical instillation, or through intravenous injection.

The bladder cancer-specific ligand PLZ4 can be used for imaging detection of non-invasive and advanced bladder cancer. Once bladder cancer has metastasized, the prognosis is poor, and cystectomy is not curative. Current imaging modalities like computed tomography (CT) and magnetic resonance imaging (MRI) are not sensitive and/or specific. While 18F-FDG-PET has been tested in clinic for staging purposes of bladder cancer, it has not been extensively used in clinic because the sensitivity and specificity are not satisfactory (Drieskens, et al., *Eur J Nucl Med Mol Imaging*, (2005) 32: 1412-1417; and Liu, et al., *Urol Int*, (2006) 77: 69-75). It is shown that by linking to NIRF Cy5.5, PLZ4 can be used for detection of subcutaneous tumor xenograft similar to metastatic bladder cancer (FIG. 5). Only 7 nmol of the cancer-specific ligand was needed for this imaging study. Cancer-specific ligand can increase the detection specificity and sensitivity of radiographic detection, thereby replacing or supplementing the costly cystoscopy procedure for diagnosis and follow-up of bladder cancer.

Dogs with naturally occurring bladder cancer can be an outstanding model to study before clinical trials in human. In most cancer studies, cancer models with tumor xenografts, usually at the subcutaneously space, are used. However, this model may not reflect what is really going on in nature. PLZ4 bound to all five canine bladder cancer cell lines tested, suggesting that naturally occurring canine bladder cancer can be used for the preclinical studies. It was also tested and found that PLZ4 could bind to primary canine bladder cancer cells freshly resected from one canine patient. Further studies will be to conduct the preclinical studies with PLZ4 in dogs with naturally occurring canine bladder cancer.

The binding specificity of PLZ4 is determined by DGR and some other amino acids. PLZ4 contains DGR. The reverse motif of RGD that binds to several integrin heterodimers including α5β3 and α5β5 (Ruoslahti, et al., *Annu Rev Cell Dev Biol*, (1996) 12: 697-715). The DGR motif was the core of the binding motif in another protein that binds to Secreted Frizzled-related proteins (Chuman, et al., *Peptides*, (2004) 25: 1831-1838). The (D/N)GR motif, also previously identified as a low-affinity integrin binding motif, was identified on the capsid of adeno-associated virus, and is important for the viral capsid-integrin 5β1 interaction and cell entry (Koivunen, et al., *J Biol Chem*, (1993) 268: 20205-20210, 1993; Koivunen, et al., *J Cell Biol*, (1994) 124: 373-380; and Asokan, et al., *J Virol*, (2006) 80: 8961-8969). PLZ4 does not bind to the parental K562 cells that express 5β1 integrin, but binds to K562 cells transfected with α5β3 integrin (FIG. 6A). IsoDGR also binds to α5β3 in tumor vaculature (Curnis, et al., *Cancer Res*, (2008) 68: 7073-7082). Several peptides contain the same DGR motif, but only PLZ4 is bladder cancer-specific. The alanine walk confirmed that, besides DGR, G (glycine, $X_6$) and F (phenylalanine, $X_7$) are important for cell binding. Change of these two amino acids abolishes or greatly diminishes the binding of PLZ4 to bladder cancer cells (FIG. 6B).

In summary, OBOC combinatorial library approach has been used to identify the PLZ4 bladder cancer-specific ligand. The clinical applications include tumor localization to guide TURBT, imaging detection and targeted drug delivery for non-invasive and metastatic bladder cancer.

Example 2: Confirmation of Canine Bladder Cancer Animal Model

Figure 7A:
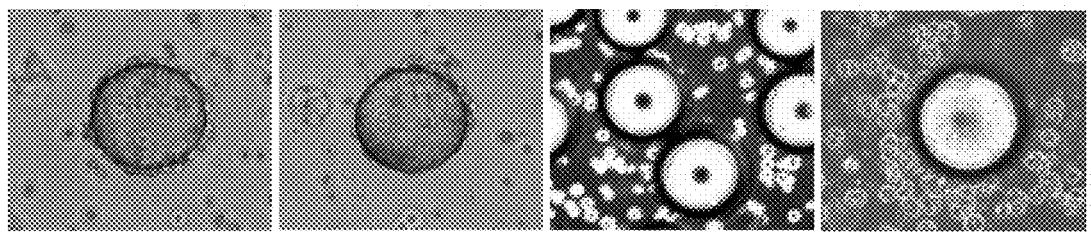
FIG. 7A-B. PLZ4 binds to Canine TCC cell lines. A. Whole cell binding assay to determine cell binding, and normal canine urothelial cell binding with PLZ4 beads. Human bladder cancer cell line 5637 and canine K9TCC-PU were trypsinzed, washed and re-suspended into single cell suspension at $10^6$ cells/ml in the complete culture medium. Normal canine bladder urothelial cells were scraped gently and digested into single cell suspension. PLZ4 beads were also washed twice with water and twice with PBS and added into the cell suspension in the 60 mm culture dish. After 60 min of gentle shaking at 37° C., the cell bindings were directly observed under inverted microscope. If PLZ4 binds to cells in solution, beads would be covered with cells exhibiting a rosette pattern under the microscope examination. This experiment was repeated 3 times for cell lines. The cell binding assay of normal canine bladder urothelial cells was repeated on 2 different dogs. a. 5637 human bladder cancer cell line; b. K9TCC-PU cell line; c. normal canine urothelial cells; d. cells from a bladder with chronic cystitis. The average diameter of the beads is 90 µm. B. Affinity fluorescence of PLZ4 peptide toward Canine TCC cell lines. Canine TCC cell lines, K9TCC-PU, K9TCC-PU-In, K9TCC-PU-AxA, K9TCC-PU-Nk and K9TCC-PU-AxC and human bladder cancer cell line 5637 were cultured on the chamber slides. The touch preparation smear was made from normal canine bladder urothelial cells from dogs euthanized for non-bladder diseases. Slides were fixed with acetone for 2 min before blocking. Cells were incubated with 1 µM of PLZ4-biotin for 1 hour at 4° C., then with streptaviding-Alexa Flour® 488 conjugate (Invitrogen, Carlsbad, Calif., USA) at 1:1000 dilution per manufacturer's protocol. After washing, the slides were mounted with DAPI containing medium for nuclear staining, and observed under converted fluorescence microscope. This experiment was repeated for 3 times. (200×)

To determine the binding of PLZ4 to canine TCC cell lines, whole cell binding assay was performed. PLZ4 was synthesized on TentaGel S NH2 resin beads (Rapp Polymere Gmbh, Germany) (Pegram, et al., *J Clin Oncol* (1998) 16:2659-2671), and incubated with single suspensions of five different canine carcinoma cell lines including K9TCC-PU, K9TCC-PU-AxA, K9TCC-PU-In, K9TCC-PU-AxC, and K9TCC-PU-Nk (kindly provided by Deborah Knapp at Purdue University, West Lafayette, Ind., USA) at $10^6$ cells/ml. The negative control was normal urothelial cells obtained from dogs that were euthanized due to non-bladder-related disorders. Human bladder cancer cell line, 5637 were served as the positive control. If PLZ4 bound to cells in suspension, then the bead surface was covered with cells. Over 95% of the bead surface was covered with 5637 and K9TCC cells (FIG. 7A-a and b, respectively). In contrast, there was no cell binding and round smooth bead surface was observed when the beads were incubated with the normal canine bladder urothelial cells (FIG. 7A-c), or bladder cells from a dog with chronic cystitis (FIG. 7A-d).

Figure 7B:
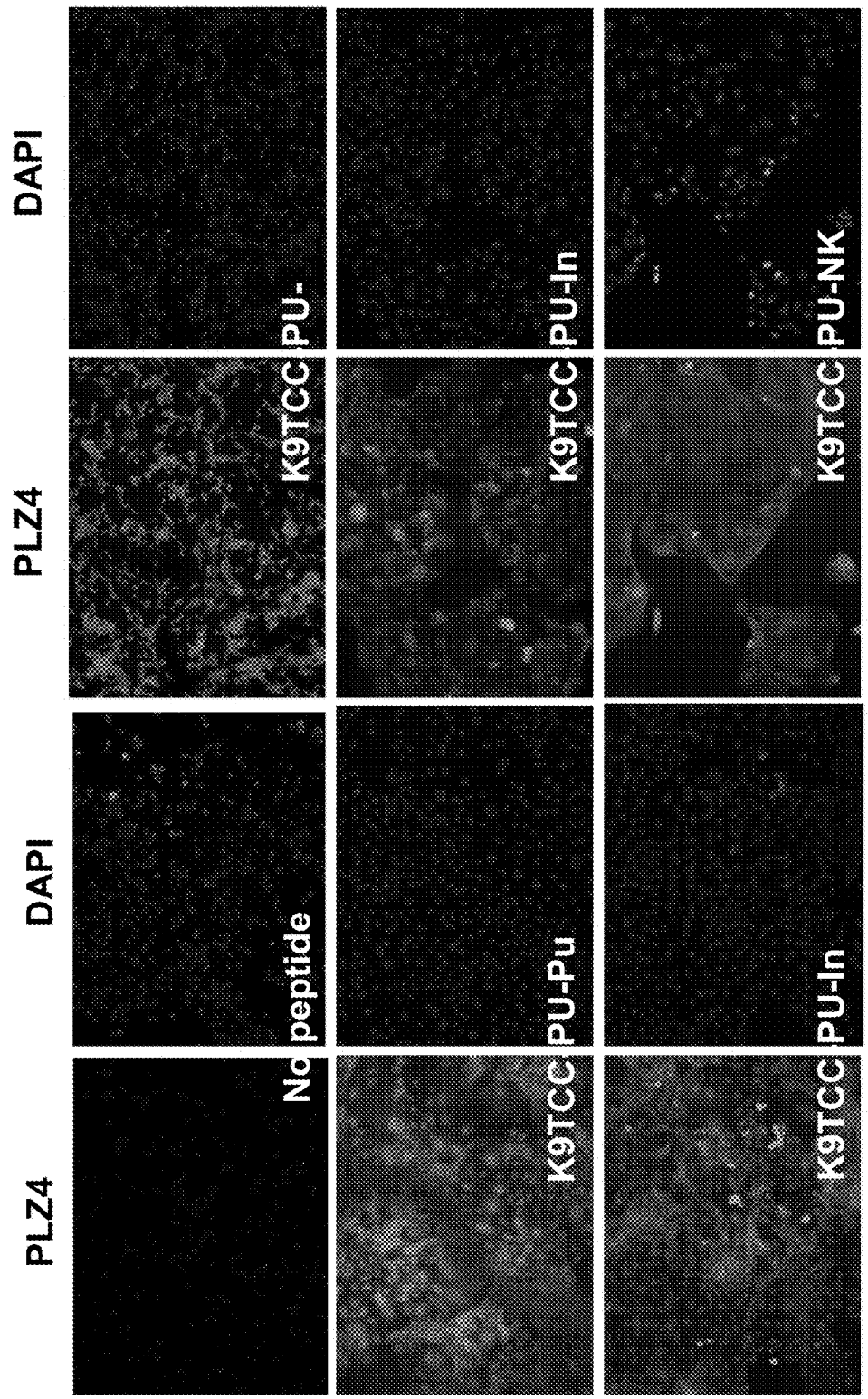

To further evaluate the binding of PLZ4 toward canine TCC cell lines, an affinity fluorescence assay was conducted. PLZ4 was synthesized and covalently conjugated to biotin. Canine TCC cell lines were cultured on chamber slides. Normal urothelial cells from dogs were prepared with touch preparation smears in which canine normal bladder tissue were touched and lightly rubbed on the surface of slides. After fixation, the slides were incubated with PLZ4-biotin and probed with streptavidin. All five canine TCC cell lines showed diffuse cell membrane staining (FIG. 7B: b-f), comparing to control without peptide incubation (FIG. 7B: a).

Figure 8A:
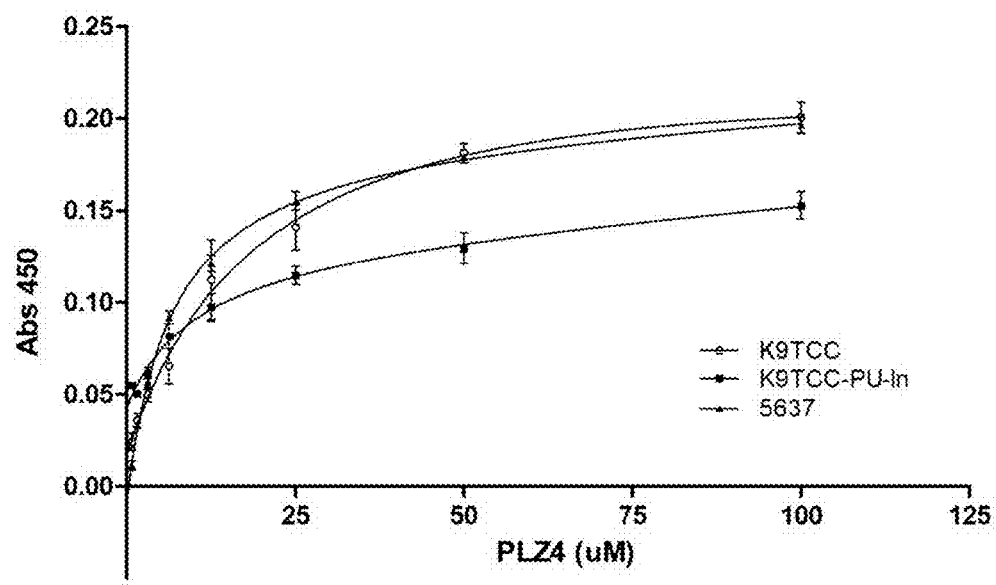
FIG. 8A-B. Binding affinity and biological effects of PLZ4 against canine TCC cell lines. A. Binding affinity of PLZ4 against K9TCC-PU and K9TCC-PU-In. Twenty thousands of K9TCC-PU and K9TCC-PU-In were seeded in 96 well plates. After culture for 24 hours, cells were fixed and incubated with different concentrations of PLZ4-biotin for 1.5 hours following avidin-HRP for another 1 hour. Cells treated with avidin-HRP only were served as background control. The color was developed using TMB substrate and read by ELISA readers. The experiment was performed in triplicates and repeated for 3 times. The mean value of the 3 experiments were shown. B. Biological effects of PLZ4 on canine TCC cell lines. Ten thousand K9TCC-PU-In and K9TCC-PU cells were seeded in the 96 well plates and treated with increasing concentrations of PLZ4 or PBS for 2 days. The cell proliferation assay was assessed by WST-8 assay per manufacturer's protocol. Cells treated with PBS were used as 100% control. Each group was performed in triplicate, repeated for 3 times. Mean values at each concentration are presented.

To further quantify the binding affinity, K9TCC-PU and K9TCC-PU-In cells were seeded in 96 well plates, fixed, and incubated with increasing concentrations of PLZ4-biotin followed by avidin-HRP. As shown in FIG. 8A, PLZ4 exhibited binding in a dose-dependent manner against canine TCC cell lines. The $Kd_{50}$ values of PLZ4 for K9TCC-PU and K9TCC-PU-In (the concentration of PLZ4 to saturate 50% of cell surface receptor) were 21.31 and 10.29 respectively.

Figure 8B:
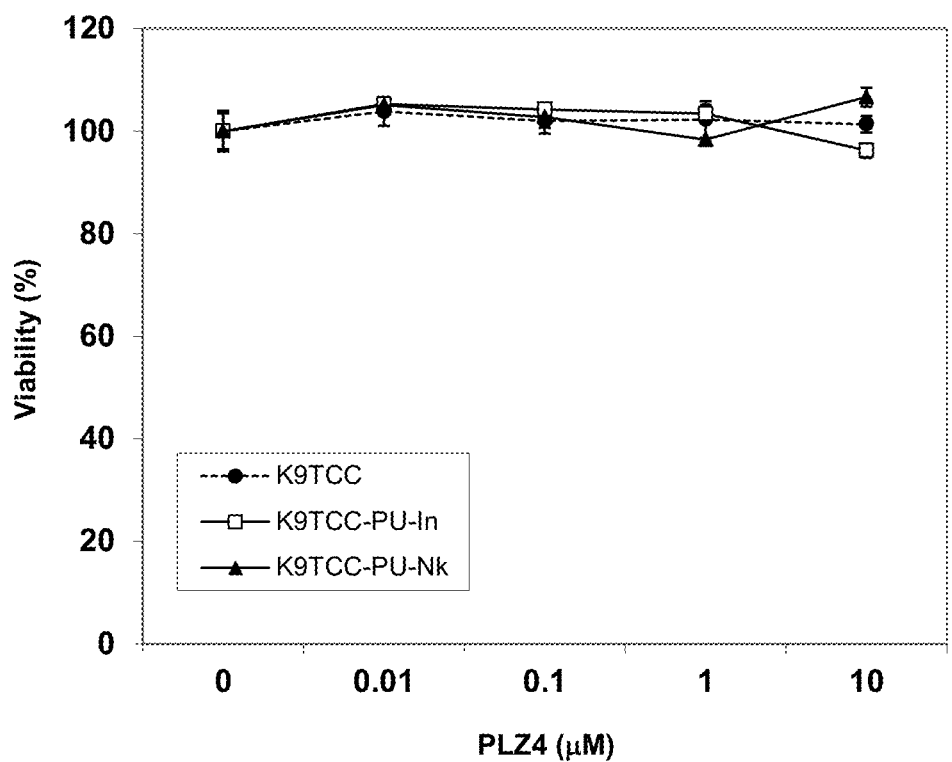

Ligand binding on the cell surface molecules may initiate cell signaling and exert biological effects on cells. The effect of PLZ4 on cell viability and proliferation was determined, as it may have potential clinical applications. K9TCC, K9TCC-PU-In and K9TCC-PU-Nk cells were seeded in 96 well plates, incubated without or with various concentrations of PLZ4 peptides. After culture with PLZ4 for 48 hours, WST-8 cell proliferation assay was performed per manufacturer's protocol (Cayman Chemical, Ann Arbor, Mich., USA). There were no significant changes in cell proliferation/viability in these three cell lines cultured with different concentration of PLZ4 when compared to cells treated with PBS control (FIG. 8B).

Figure 9A:
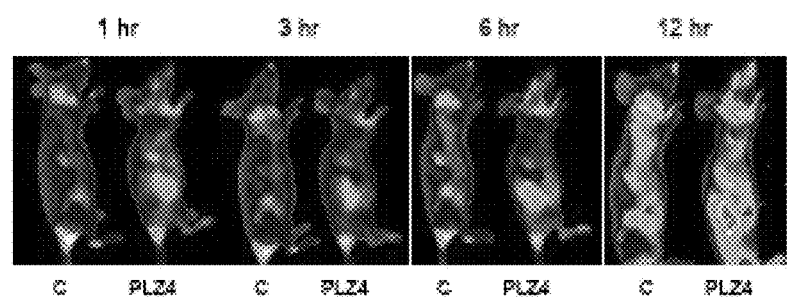
FIG. 9A-C. Homing of PLZ4 to mouse xenograft of canine bladder cancers. A. In vivo imaging of canine K9TCC-PU-In xenografts with PLZ4. Upper panel: in vivo near-infrared fluorescence images were taken at different time points after injection. B: the control mouse that received Streptavidine-Cy5.5. PLZ4: the mouse that received PLZ4-Cy5.5. Red arrows point to tumor xenografts. Lower panel: ex vivo imaging of organs for fluorescence intensity. Specific uptake of fluorescence was observed in tumor xenografts from mice that received PLZ4-Cy5.5. Non-specific uptake in kidney and liver was also observed in the control mouse and in the mouse that received PLZ4-Cy5.5. C. Ex vivo quantitative analysis of fluorescence uptake in tumor xenografts. The fluorescence intensity of tumor xenografts was normalized to that of the liver and kidney of the same mice (the normalized value of liver and kidney is defined as 1.0). After normalization, uptake of tumor xenografts from mice that received PLZ4-Cy5.5 was much higher than the uptake of xenografts from the control mice (p=0.003 and p<0.001 for the values normalized with, respectively).
Figure 9B:
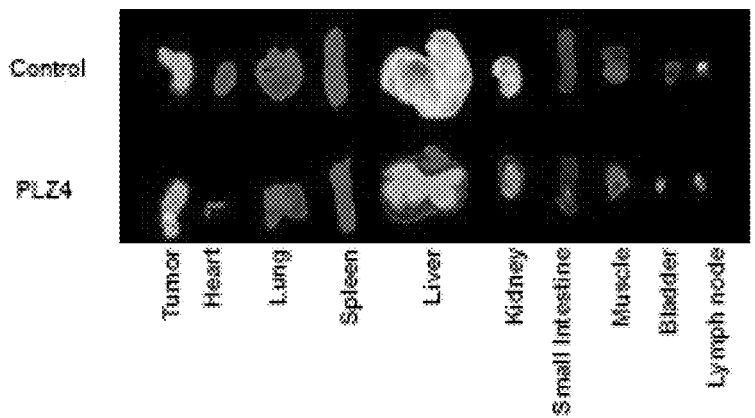

The tumor-specific homing/targeting property and in vivo biodistribution/binding specificity of PLZ4 on a canine TCC xenograft mouse model was also determined. TCC-PU-In cells mixed with Matrigel were implanted into 8-week-old nude mice for 3-4 weeks. When the xenografts were at the size of 0.5-0.8 cm in diameter, mice were randomly selected to be injected with 100 μl (7 nmol) of pre-incubated PLZ4-biotin-streptavidin-Cy5.5 complex or streptavidin-Cy5.5 dye under anesthesia. Total body images were collected at 0, 1, 3, 6, and 12 hours after injection (FIG. 9a). Substantial accumulation of signals was accumulated at the tumor site in the mouse injected with PLZ4-Cy5.5 complex in a time-dependent manner with a maximum signal observed at 12 hours. In contrast, negligible fluorescence uptake of Cy5.5 dye by tumors was detected in the control mice receiving streptavidin-Cy5.5. To determine if there were any other vital organs non-specifically taking up the injected dye complex, mice were euthanized at 12 hours after injection, vital organs and cancer xenografts were removed for ex vivo imaging. Both liver and kidney demonstrated considerable signals even in the control mice that received streptavidin-Cy5.5, suggesting the non-specific uptake (FIG. 9A). Compared with the tumor xenografts from the control mice treated with streptavidin-Cy5.5, xenografts from the mice that received PLZ4-Cy5.5 accumulated significantly higher fluorescence signals after normalizing the fluorescence to liver (3.2 times, p=0.003) and kidney (3.8 times, p<0.001) (FIG. 9B). No significant fluorescence uptake was observed in other organs including bladder. Collectively, these data demonstrated that PLZ4 exhibited excellent homing property toward TCC xenograft in vivo.

Figure 9C:
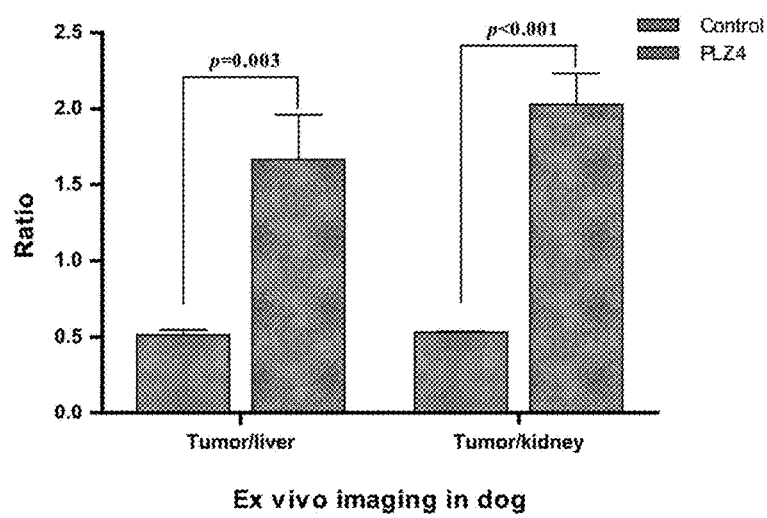

The present study shows that a human bladder cancer-specific ligand can also target canine bladder TCC cells. These findings are not only important for the drug development for human applications, but also for the diagnosis and treatment of canine bladder cancer. One major issue encountered during the drug development for human application is the lack of appropriate animal models. Immunocompromised mice with tumor xenografts are most often used instead. Physiologically, mouse xenograft models are radically different from naturally occurring cancer in human patients. The most commonly used xenograft model is subcutaneous xenografts while most human cancers, even at the very late stage, rarely metastasize to the subcutaneous space. Furthermore, because of the rapid tumor formation (weeks) in xenograft models, the local vasculature formation and permeability can be dramatically different from that of naturally occurring cancer that may take months to years to develop. The present study shows that PLZ4 can also bind to canine bladder cancer cells both in vitro and in vivo (FIGS. 7 and 9). It was also found that PLZ4 could bind to cancer cells from one canine bladder TCC clinical specimen, but not to a bladder lymphoid hyperplasia specimen from another clinical dog (data not shown).

The present findings suggest that the preclinical studies of the bladder cancer specific ligands can be performed in dogs with naturally occurring bladder cancer.

One major application of PLZ4 is local visualization of bladder cancer during transurethral resection of bladder cancer (TURBT). Local visualization of bladder cancer is clinically relevant since incomplete resection is seen in up to one third of cases after TURBT that contributes to the high recurrence of bladder cancer after therapy. Fluorescence cystoscopy with 5-Aminolevulinic acid (ALA) has been used for this purpose (Daniltchenko, et al. *J Urol* (2005) 174:2129-2133). But nonspecific uptake of ALA by non-cancer urothelial cells, especially in inflamed bladder, preclude its wide clinical application. Our previous findings showed that PLZ4 could bind to bladder cancer cells in urine at pH 6.0, and that PLZ4 did not bind to cells collected from the urine specimens of patients who were actively treated with Bacillus Calmette-Guérin. Therefore, PLZ4 conjugated to a fluorescent dye is an excellent candidate for this application. The orthotopic mouse bladder cancer models have been developed. Because of the size limitation, the preclinical studies with cystoscopy in mice (even in rats) may not be possible. Cystoscopy has been routinely performed for the diagnosis of bladder disorders in dogs. The $Kd_{50}$ of PLZ4 at 10.29 and 21.31 μM can be easily achievable with local intravesical instillation.

Another application of PLZ4 is imaging detection of bladder cancer that can supplement or decrease intrusive and costly cystoscopy. MicroMRI and microPET can be performed in mice. Because of the tiny size of orthotopic mouse bladder cancer models, the discriminations of sizes, numbers and locations of tumor in mice may not be at all possible and not translatable to human patients. Furthermore, because of the proximal location of bladder to external imaging device, little tissue absorption and scattering, the imaging studies in mice are not applicable to those in large animals like human patients. Both MRI and PET scans have been widely used for the diagnosis of canine malignancies. Therefore, it can be determined if MRI and PET or SPECT can be used to facilitate the detection of bladder cancer using PLZ4 conjugated to imaging agents, such as iron oxide for MRI and radioisotope for PET/SPECT. In the present in vivo studies (FIG. 9), only 7 nmol (equivalent to 20 mg of PLZ4 in a 75-Kg patient) of PLZ4-Cy5.5 was used, and little non-specific uptake was observed. This is consistent with our previous findings that PLZ4 only bought to one of 12 human cell lines with different tissue/cancer origins, and did not bind to any of the confounding cells that possibly exist inside bladder such as normal urothelilal cells, whole blood, peripheral blood mononuclear cells (PBMC), fibroblasts, and vascular endothelial cells. This specific binding is useful for in vivo targeting with PLZ4 conjugates.

In summary, the present human bladder cancer-specific ligands, illustrated by PLZ4, can also bind to canine bladder cancer cells. Therefore, the preclinical studies of PLZ4 as a human diagnostic and therapeutic agent can be performed in dogs with naturally occurring bladder TCC. The human bladder cancer-specific ligands described herein, illustrated by PLZ4, also can be used in the management of canine bladder cancer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING

SEQ ID NO:1—$X_1DGRX_5GF$, wherein $X_1$ is any amino acid other than cysteine (i.e., A, D, E, F, G, H, I, K, L, M, N, P, Q, R, S, T, V, W, Y); $X_5$ is any amino acid other than cysteine (A, D, E, F, G, H, I, K, L, M, N, P, Q, R, S, T, V, W, Y).

SEQ ID NO:2—$X_1DGRX_5GF$, wherein $X_1$ is Gln, Gly or Ala; $X_5$ is any amino acid other than cysteine (i.e., A, D, E, F, G, H, I, K, L, M, N, P, Q, R, S, T, V, W, Y).

SEQ ID NO:3—$X_1DGRX_5GF$, wherein $X_1$ is any amino acid; $X_5$ is Met, Lys, Gly, Ala or Gly-Gly.

SEQ ID NO:4—$X_1DGRX_5GF$, wherein $X_1$ is Gln, Gly or Ala; $X_5$ is Met, Lys, Gly, Ala or Gly-Gly.

SEQ ID NO:5—QDGRMGF

SEQ ID NO:6—QDGRKGF

SEQ ID NO:7—$QDGRK_GGF$, wherein $K_G$ refers to a lysine residue with a glycine residue attached to its side chain.

SEQ ID NO:8—$X_{(1-5)}X_6DGRX_7GFX_{(8-12)}$, wherein $X_{(1-5)}$ and $X_{(8-12)}$ are not present or any amino acid (i.e., A, C, D, E, F, G, H, I, K, L, M, N, P, Q, R, S, T, V, W, Y); $X_6$ and $X_7$ are any amino acid other than cysteine (i.e., A, D, E, F, G, H, I, K, L, M, N, P, Q, R, S, T, V, W, Y).

SEQ ID NO:9—$X_1X_2X_3DGRX_4GFX_5X_6$, wherein $X_1$, $X_2$, $X_5$, $X_6$ are not present or any amino acid (i.e., A, C, D, E, F, G, H, I, K, L, M, N, P, Q, R, S, T, V, W, Y); $X_3$ and $X_4$ are any amino acid other than cysteine (i.e., A, D, E, F, G, H, I, K, L, M, N, P, Q, R, S, T, V, W, Y).

SEQ ID NO:10—$cX_1DGRX_5GFc$, wherein $X_1$ is any amino acid other than cysteine (i.e., A, D, E, F, G, H, I, K, L, M, N, P, Q, R, S, T, V, W, Y); $X_5$ is any amino acid other than cysteine (i.e., A, D, E, F, G, H, I, K, L, M, N, P, Q, R, S, T, V, W, Y), and c is D-cysteine.

SEQ ID NO:11—cQDGRKGFc, wherein c is D-cysteine.

SEQ ID NO:12—cQDGRMGFc, wherein c is D-cysteine.

SEQ ID NO:13—$cQDGRK_{(G1-6)}Fc$, wherein c is D-cysteine, wherein $K_{(G1-6)}$ refers to a lysine residue with one to six glycine residues attached to its side chain.

SEQ ID NO:14—CQDGRMGFC

SEQ ID NO:15—$cX_1X_2X_3X_4X_5X_6X_7c$, wherein X is any natural L-amino acid except cysteine (i.e., A, D, E, F, G, H, I, K, L, M, N, P, Q, R, S, T, V, W, Y); and c is D-cysteine.

SEQ ID NO:16—$c(U/Z)_1(U/Z)_2(U/Z)_3(U/Z)_4(U/Z)_5c$—wherein U is an unnatural amino acid and Z is any natural L-amino acid except arginine, cysteine and lysine (i.e., A, D, E, F, G, H, I, L, M, N, P, Q, S, T, V, W, Y).

SEQ ID NO:17—$CX_1DGRX_5GFC$, wherein $X_1$ and $X_5$ are any amino acid other than cysteine (e.g., A, D, E, F, G, H, I, K, L, M, N, P, Q, R, S, T, V, W, Y).

What is claimed is:

1. A method of delaying, blocking, inhibiting, and/or reducing the growth, migration and metastasis of a bladder cancer cell in a subject in need thereof, comprising contacting bladder tissue with a peptide, linked to a therapeutic moiety;
wherein the peptide comprises the amino acid sequence $X_1DGRX_5GF$ (SEQ ID NO:2), wherein $X_1$ is selected from Gln and Gly and $X_5$ is any amino acid other than cysteine, wherein the peptide is no longer than 25 amino acids in length, and binds to bladder cancer cells, and is recombinant and/or synthetic;
wherein the peptide binds to bladder cancer cells and the therapeutic moiety delays, blocks, inhibits and/or reduces the growth, migration, and metastasis of the bladder cancer cells.

2. The method of claim 1, wherein $X_5$ is Met, Lys, Gly, Ala or Gly-Gly.

3. The method of claim 1, wherein the peptide comprises an amino acid sequence selected from the group consisting of QDGRMGF (SEQ ID NO:5), QDGRKGF (SEQ ID NO:6), and QDGRK$_G$GF (SEQ ID NO:7).

4. The method of claim 1, wherein the peptide does not bind to normal bladder tissue.

5. The method of claim 1, wherein the peptide further comprises from 1 to 5 flaking amino acid residues at the amino and/or carboxyl termini.

6. The method of claim 1, wherein the peptide further comprises a cysteine residue at the amino terminus and a cysteine residue at the carboxyl terminus.

7. The method of claim 1, wherein the peptide is no longer than 10 amino acids in length.

8. The method of claim 1, wherein the peptide is circularized.

9. The method of claim 1, wherein the peptide is formulated as a nanoparticle.

10. The method of claim 1, wherein the peptide is a magnetic nanoparticle-peptide conjugate.

11. The method of claim 1, wherein the subject is a mammal.

12. The method of claim 1, wherein the subject is in remission and/or has undergone the removal of a primary tumor.

13. The method of claim 1, wherein the therapeutic moiety is an Fc portion of an IgG, a cytotoxin, an anticancer agent, or a radioisotope.

14. The method of claim 1, wherein the peptide linked to the therapeutic moiety is administered to the subject intravenously, intratumorally, intraurethrally or via intravesical instillation.

15. A method of delaying, blocking, inhibiting, and/or reducing the growth, migration and metastasis of a bladder cancer cell in a subject in need thereof, comprising contacting the bladder cancer cell with a peptide comprising the amino acid sequence $X_1DGRX_5GF$,
wherein $X_1$ is selected from Gln and Gly and $X_5$ is any amino acid other than cysteine, wherein the peptide is no longer than 10 amino acids in length and is recombinant and/or synthetic, wherein the peptide is linked to a therapeutic moiety, wherein the peptide binds to bladder cancer cells and the therapeutic moiety delays, blocks, inhibits and/or reduces the growth, migration and metastasis of the bladder cancer cells.

16. The method of claim 15, wherein $X_5$ is Met, Lys, Gly, Ala or Gly-Gly.

17. The method of claim 15, wherein the peptide comprises an amino acid sequence selected from the group consisting of QDGRMGF (SEQ ID NO:5), QDGRKGF (SEQ ID NO:6), and QDGRK$_G$GF (SEQ ID NO:7).

18. The method of claim 15, wherein the peptide does not bind to normal bladder tissue.

19. The method of claim 15, wherein the peptide further comprises from 1 to 5 flaking amino acid residues at the amino and/or carboxyl termini.

20. The method of claim 15, wherein the peptide further comprises a cysteine residue at the amino terminus and a cysteine residue at the carboxyl terminus.

21. The method of claim 15, wherein the peptide is circularized.

22. The method of claim 15, wherein the peptide is formulated as a nanoparticle.

23. The method of claim 15, wherein the peptide is a magnetic nanoparticle-peptide conjugate.

24. The method of claim 15, wherein the subject is a mammal.

25. The method of claim 15, wherein the subject is in remission and/or has undergone the removal of a primary tumor.

26. The method of claim 15, wherein the therapeutic moiety is an Fc portion of an IgG, a cytotoxin, an anticancer agent, or a radioisotope.

27. The method of claim 15, wherein the peptide linked to the therapeutic moiety is administered to the subject intravenously, intratumorally, intraurethrally or via intravesical instillation.

28. A method of delaying, blocking, inhibiting, and/or reducing the growth, migration and metastasis of a bladder cancer cell in a subject in need thereof, comprising contacting bladder tissue with a peptide, linked to a therapeutic moiety;
wherein the peptide comprises the amino acid sequence $X_1$DGRX$_5$GF (SEQ ID NO:2), wherein $X_1$ is selected from Gln, Gly and Ala and $X_5$ is any amino acid other than cysteine, and the peptide comprises one or more of:
  i) one or more of the amino acid residues are D-amino acids;
  ii) protecting groups at one or both of the N-terminus and the C-terminus;
  iii) two or more repeats of the amino acid sequence $X_1$DGRX$_5$GF (SEQ ID NO:2), wherein $X_1$ is selected from Gln, Gly and Ala and $X_5$ is any amino acid other than cysteine; and
  iv) one or both of an N-terminal D-cysteine and a C-terminal D-cysteine and is circularized
wherein the peptide does not comprise a combination of ii) and iv), is no longer than 25 amino acids in length, binds to bladder cancer cells, and is recombinant and/or synthetic; and
wherein the peptide binds to bladder cancer cells and the therapeutic moiety delays, blocks, inhibits and/or reduces the growth, migration, and metastasis of the bladder cancer cells.

29. The method of claim 28, wherein $X_5$ is Met, Lys, Gly, Ala or Gly-Gly.

30. The method of claim 28, wherein the peptide comprises an amino acid sequence selected from the group consisting of QDGRMGF (SEQ ID NO:5), QDGRKGF (SEQ ID NO:6), and QDGRK$_G$GF (SEQ ID NO:7).

31. The method of claim 28, wherein the peptide does not bind to normal bladder tissue.

32. The method of claim 28 i)-iii), wherein the peptide further comprises from 1 to 5 flaking amino acid residues at the amino and/or carboxyl termini.

33. The method of claim 28 i)-iii), wherein the peptide further comprises a cysteine residue at the amino terminus and a cysteine residue at the carboxyl terminus.

34. The method of claim 28, wherein the peptide is no longer than 10 amino acids in length.

35. The method of claim 28, wherein the peptide is formulated as a nanoparticle.

36. The method of claim 28, wherein the peptide is a magnetic nanoparticle-peptide conjugate.

37. The method of claim 28, wherein the subject is a mammal.

38. The method of claim 28, wherein the subject is in remission and/or has undergone the removal of a primary tumor.

39. The method of claim 28, wherein the therapeutic moiety is an Fc portion of an IgG, a cytotoxin, an anticancer agent, or a radioisotope.

40. The method of claim 28, wherein the peptide linked to the therapeutic moiety is administered to the subject intravenously, intratumorally, intraurethrally or via intravesical instillation.

* * * * *